(12) United States Patent
Desire

(10) Patent No.: US 7,790,864 B2
(45) Date of Patent: Sep. 7, 2010

(54) ANTIBODY TO BACE455, AN ALTERNATIVE SPLICE VARIANT OF THE HUMAN BETA-SECRETASE

(75) Inventor: Laurent Desire, Paris (FR)

(73) Assignee: Exonhit Therapeutics SA, Paris (FR)

( * ) Notice: Subject to any disclaimer, the term of this patent is extended or adjusted under 35 U.S.C. 154(b) by 0 days.

(21) Appl. No.: 10/578,493

(22) PCT Filed: Nov. 5, 2004

(86) PCT No.: PCT/IB2004/003897

§ 371 (c)(1),
(2), (4) Date: May 5, 2006

(87) PCT Pub. No.: WO2005/045021

PCT Pub. Date: May 19, 2005

(65) Prior Publication Data

US 2007/0142277 A1 Jun. 21, 2007

Related U.S. Application Data

(60) Provisional application No. 60/517,401, filed on Nov. 6, 2003.

(51) Int. Cl.
*C07K 16/00* (2006.01)
*C12P 21/08* (2006.01)
*A61K 39/395* (2006.01)

(52) U.S. Cl. .............. 530/388.24; 530/388.1; 530/388.15; 530/387.9; 530/387.3; 530/387.1; 424/130.1; 424/141.1; 424/145.1

(58) Field of Classification Search .............. None
See application file for complete search history.

(56) References Cited

U.S. PATENT DOCUMENTS 6,420,534 B1 * 7/2002 Gurney et al. ............... 435/226
6,583,275 B1 * 6/2003 Doucette-Stamm et al. ...... 536/23.1

OTHER PUBLICATIONS

Redehasse et al., 1989, Nature, vol. 337 (6208), pp. 651-653.*

Salanoubat, et al., "Genome Sequence of the Plant Pathogen *Ralstonia solanacearum*", Nature, vol. 415, No. 6871, p. 497-502, Jan. 31, 2002.

EMBL Accession No. AAE04797, Sep. 10, 2001, "Human Aspartyl Protease (ASP-2) from clone 1869868."

Fujiwara, et al., "Neutrophil Elastase: A Candidate Antigen for Adoptive T Cell Therapy for Myeloid Leukemia?", Blood, vol. 100, No. 11, Nov. 16, 2002, p. 677a, Abstract No. 2666, 44th Annual Meeting of the American Society of Hematology, Philadelphia, PA, USA; Dec. 6-10, 2002.

Zohar, et al., "Quantification and Distribution of β-secretase Alternative Splice Variants in the Rat and Human Brian", Molecular Brain Research, vol. 115, p. 63-68, 2003.

Tanahashi, et al., "Three Novel Alternatively Spliced Isoforms of the Human Beta-Site Amyloid Precursor Protein Cleaving Enzyme (BACE) and their Effect on Amyloid Beta-Peptide Production", Neuroscience Letters, vol. 307, p. 9-12, 2001.

Ehehalt, et al., "Splice Variants of the β-Site APP-cleaving Enzyme BACE1 in Human Brain and Pancreas", Biochemical and Biophysical Research Communications, vol. 293, p. 30-37, 2002.

Turner III, et al., "Subsite Specificity of Memapsin 2 (β-Secretase): Implications for Inhibitor Design", Biochemistry, vol. 40, No. 34, p. 10001-10006, 2001.

Hom, et al., "Design and Synthesis of Statine-Based Cell-Permeable Peptidomimetic Inhibitors of Human β-Secretase", J. Med. Chem., vol. 46, p. 1799-1802, 2003.

* cited by examiner

*Primary Examiner*—Olga N Chernyshev
(74) *Attorney, Agent, or Firm*—Hunton & Williams LLP

(57) ABSTRACT

The present invention relates generally to the fields of genetics, biochemistry, medicinal chemistry and medicine. The present invention more particularly discloses the identification of a human gene variant involved in neuropathological conditions, and methods for the diagnosis, prevention and treatment of such diseases and related disorders, as well as for the screening of therapeutically active drugs. The present invention relates to catalytically active beta-secretase (Memapsin2, BACE) variants, and nucleic acids encoding them. The invention is useful in the identification of agents that inhibit the activity of a particular BACE isoform and thus agents and therapies affecting the genesis, development or progression of neuropathological conditions, including Alzheimer's disease and dementia.

1 Claim, 5 Drawing Sheets

FIGURE 1A

```
   1 atggccaag cctgcctg gctcctgctg tggatgggcg cgggagtgct
  51 gcctgccac ggcaccaga acggcatccg gctgcccctg cgcagcgggc
 101 tgggggcgc cccctggg ctgcgctgc cccggagac cgacgaagag
 151 ccggagagc ccggccggag ggcagcttt gtggacggag tggacaacct
 201 gagggcaag tcggcagg gctactacgt ggatgacc gtggcagcc
 251 cccgagac gtcaacatc ctggtggata caggcagcag taactttgca
 301 gtggtgctg cccccacc cttcctgcat cgctactac agagccagct
 351 gtccagcaca tacgggacc tcggaaggg tgtgtatgtg ccctacacc
 401 aggcaagtg ggaaggggag ctgggcaccg acctggtaag catccccat
 451 ggcccaaacg tcactgtgcg tgccacatt gctgcctca ctgaatcaga
 501 caagttcttc atcaacggct ccactgggga aggcatcctg ggctggct
 551 atgctgagat tgccagatc attgaggta tgaccactc gctgtacaca
 601 tgagtctct ggtatacacc catccgcgg gagtggtatt atgaggtcat
 651 cattgtgcgg gtggagatca atggacagga tctgaaaatg gactgcaagg
 701 agtacaacta tgacaagagc attgtggaca gtggcaccac caacctcgt
 751 ttgcccaaga aagtgtttga agtgcagtc aaatccatca aggcagcctc
 801 ctccacggag aagttcctg atggtttctg gctaggagag cagctggtgt
 851 gctgccaagc aggcaccacc cctgggaaca tttccccagt catctcacto
 901 tacctaatgg gtgaggttac caaccagtcc ttccgcatca ccatcctcc
 951 gcagcaatac ctgcggcag tggaagatgt ggccactgcc caagacgact
1001 gttacaagtt tgccatctca cagtcatcca cggcactgt tatggcagct
1051 gttatcatgg agggcttcta cgttgtcttt gatcgggccc gaaaacgaat
1101 tggcttcgct gtcagcgctt gccatgtgca cgatgagttc aggacggcag
1151 cggtggaagg cctttttgtc acctggaca tggaagactg tgctacaac
1201 attcccaaga cagatgagtc aacctcatg accatagct atgtcatggc
1251 tgccatctgc gcctcttca tgctggcact ctgctcatg gtgtgtcagt
1301 ggcgctgcct ccgtgcctg cgccagcagc atgatgactt tgctgatgac
1351 atctccctgc tgaagtga
```

FIGURE 1B

```
BACE501:   1 MAQALPWLLLWMGAGVLPAHGTQHGIRLPLRSGLQGAPLGLRLPRETDEEPEEPGRRGSF  60
             MAQALPWLLLWMGAGVLPAHGTQHGIRLPLRSGLQGAPLGLRLPRETDEEPEEPGRRGSF
BACE455:   1 MAQALPWLLLWMGAGVLPAHGTQHGIRLPLRSGLQGAPLGLRLPRETDEEPEEPGRRGSF  60

BACE501:  61 VEMVDNLRGKSGQGYYVEMTVGSPPQTLNILVDTGSSNFAVGAAPHPFLHRYYQRQLSST 120
             VEMVDNLRGKSGQGYYVEMTVGSPPQTLNILVDTGSSNFAVGAAPHPFLHRYYQRQLSST
BACE455:  61 VEMVDNLRGKSGQGYYVEMTVGSPPQTLNILVDTGSSNFAVGAAPHPFLHRYYQRQLSST 120

BACE501: 121 YRDLRKGVYVPYTQGKWEGELGTDLVSIPHGPNVTVRANIAAITESDKFFINGSNWEGIL 180
             YRDLRKGVYVPYTQGKWEGELGTDLVSIPHGPNVTVRANIAAITESDKFFINGSNWEGIL
BACE455: 121 YRDLRKGVYVPYTQGKWEGELGTDLVSIPHGPNVTVRANIAAITESDKFFINGSNWEGIL 180

BACE501: 181 GLAYAEIARPDDSLEPFFDSLVKQTHVPNLFSLQLCGAGFPLNQSEVLASVGGSMIISGI 240
             GLAYAEIAR                                             IISGI
BACE455: 181 GLAYAEIAR--------------------------------------------IISGI 194

BACE501: 241 DHSLYTGSLWYTPIRREWYYEVIIVRVEINGQDLKMDCKEYNYDKSIVDSGTTNLRLPKK 300
             DHSLYTGSLWYTPIRREWYYEVIIVRVEINGQDLKMDCKEYNYDKSIVDSGTTNLRLPKK
BACE455: 195 DHSLYTGSLWYTPIRREWYYEVIIVRVEINGQDLKMDCKEYNYDKSIVDSGTTNLRLPKK 254

BACE501: 301 VFEAAVKSIKAASSTEKFPDGFWLGEQLVCWQAGTTPWNIFPVISLYLMGEVTNQSFRIT 360
             VFEAAVKSIKAASSTEKFPDGFWLGEQLVCWQAGTTPWNIFPVISLYLMGEVTNQSFRIT
BACE455: 255 VFEAAVKSIKAASSTEKFPDGFWLGEQLVCWQAGTTPWNIFPVISLYLMGEVTNQSFRIT 314

BACE501: 361 ILPQQYLRFVEDVATSQDDCYKFAISQSSTGTVMGAVIMEGFYVVFDRARKRIGFAVSAC 420
             ILPQQYLRFVEDVATSQDDCYKFAISQSSTGTVMGAVIMEGFYVVFDRARKRIGFAVSAC
BACE455: 315 ILPQQYLRFVEDVATSQDDCYKFAISQSSTGTVMGAVIMEGFYVVFDRARKRIGFAVSAC 374

BACE501: 421 HVHDEFRTAAVEGPFVTLDMEDCGYNIPQTDESTLMTIAYVMAAICALFMLPLCLMVCQW 480
             HVHDEFRTAAVEGPFVTLDMEDCGYNIPQTDESTLMTIAYVMAAICALFMLPLCLMVCQW
BACE455: 375 HVHDEFRTAAVEGPFVTLDMEDCGYNIPQTDESTLMTIAYVMAAICALFMLPLCLMVCQW 434

BACE501: 481 RCLRCLRQQHDDFADDISLLK 501
             RCLRCLRQQHDDFADDISLLK
BACE455: 435 RCLRCLRQQHDDFADDISLLK 455
```

ANTIBODY TO BACE455, AN ALTERNATIVE SPLICE VARIANT OF THE HUMAN BETA-SECRETASE

CROSS-REFERENCE TO RELATED APPLICATIONS

This application is the U.S. national stage application of International Application No. PCT/IB2004/003897, filed on Nov. 5, 2004, which claims the benefit of U.S. Provisional Application No. 60/517,401, filed Nov. 6, 2003, the disclosures of each of which are herein incorporated by reference in their entireties.

FIELD OF THE INVENTION

The present invention relates generally to the fields of genetics, biochemistry, medicinal chemistry and medicine. The present invention more particularly discloses the identification of a human gene variant involved in neuropathological conditions, and methods for the diagnosis, prevention and treatment of such diseases and related disorders, as well as for the screening of therapeutically active drugs. The present invention relates to catalytically active beta-secretase (Memapsin2, BACE) variants, and nucleic acids encoding them. The invention is useful in the identification of agents that inhibit the activity of a particular BACE isoform and thus agents and therapies affecting the genesis, development or progression of neuropathological conditions, including Alzheimer's disease and dementia.

BACKGROUND OF THE INVENTION

The importance of alternative RNA splicing in the generation of genetic diversity is now widely recognized as one of the most important ways (along with the use of alternative promoters and alternative polyadenylation) for a single gene to encode more than one mRNA transcript. The pre-mRNA or mRNA isoforms that result from alternative splicing may differ in stability, translatability, or protein sequence encoded, each of which may alter the function of the encoded protein.

This can be best exemplified in the field of apoptosis (Jiang and Wu., Proc. Soc. Exp. Biol. Med. 220: 64-72 (1999)). Alterations in alternative splicing, in particular mutations of the canonical sequences at the intron/exon border, may cause abnormal splicing patterns that affect gene expression and cause disease. Cooper et al. (1998) recently showed that at least 10% of human inherited diseases involve mutations that create an RNA splicing defect; see e.g., Cooper et al., Nucleic Acids Res. 26: 285-287 (1998).

Sporadic mutations in the consensus splicing signals are observed in a wide-range of pathologies such as cancers, neurodegenerative disorders, inflammation/asthma and other metabolic diseases. The RNA splicing defects can include exon skipping, intron retention and new splicing events due to the use of cryptic splicing sites or the creation of new splicing consensus sequences (Lopez, Annu. Rev. Genet. 32: 279-305 (1998)). Alterations in activity, levels, or amino acid sequence of cellular splicing factors may affect the efficiency of splicing or the regulation of alternative splicing. For example, the presence of a single nucleotide in the nucleotide sequence of the Survival Motor Neuron gene regulates the splicing of this gene, and is responsible for spinal muscular atrophy (Lorson et al. Proc. Natl. Acad. Sci. USA, 96: 6307-6311 (1999)). In human brains taken from patients with sporadic Alzheimer's disease, splicing events including a) alterations in the amino acid sequence of the protein presinilin-1 (PS1), caused by a deletion of exon 9 of the ps1 gene, b) deletion of exon 5 of the gene encoding presenilin 2 (the ps2 gene), and c) (in cases of sporadic frontotemporal dementia) aberrant splicing of exon 5 of the ps2 gene have been be implicated in the neuropathology (Isoe-Wada. et al. Eur J Neurol, 6, 163-167 (1999); Sato et al. J. Biol. Chem. 276: 2108-2114 (1991)).

Alzheimer's disease (AD) is a devastative degenerative disorder of the brain with important formation of amyloid plaques, neurofibrillary tangles, gliosis and neuronal loss (Hardy et al. Nat. Neurosci 1:355-358 (1998); Selkoe, D. J. In: Alzheimer disease, Ed 2 (Terry, R. D., Katzman, R., Bick, K. L., Sisodia, S. S., eds), pp 293-310. Philadelphia: Lippincott Williams and Wilkins. (1999)). The most affected regions are cortex, hippocampus, subiculum, hippocampal gyrus, and amygdala. Patients suffering from AD have increased problems with memory loss, intellectual functions and skills, personality changes and schizophrenia. AD is the leading cause of dementia in elderly persons and there is no effective palliative or preventive treatment for the neurodegeneration.

Several genetic and epigenetic factors have been suggested as mechanisms contributing to AD; these include genetic predisposition, infectious agents, toxins, metals, head trauma and vascular dementia. Globally, it is the dysregulation of intracellular pathways responsible for amyloid precursor protein (APP) proteolytic processing that results in enhanced formation of a peptide termed A-Beta (A-β) 1-42—a form of the A-β peptide which is particularly amyloidogenic, which now appears to be central to the pathophysiology of AD (Selkoe, Neuron 32: 177-180 (2001).

The A-β peptide is also the primary protein constituent in cerebrovascular amyloid deposits. Amyloid is a filamentous material that is arranged in beta-pleated sheets. The A-β peptide is a hydrophobic peptide comprising up to 43 amino acids. A-β peptide has been shown to be toxic to neurons in a number of ways, including by the induction of reactive oxygen species (ROS), induction of altered gene transcription, causing increased susceptibility to excitotoxicity, and other processes commonly associated with neurodegenerative conditions ((Ramsden et al., J. Neurochem. 79: 699-712 (2001); Shukla et al., J. Cell. Path. 5: 241-249 (2002); Green and Peers, Neurochem. 77: 953-956 (2001); Kowall et al., Neurobiol. Aging 13: 537-542 (1992); MacManus et al., J. Biol. Chem. 275: 4713-4718 (2000)). Mutations in APP, Presenilin 1 and 2 (PS1 and PS2, respectively) greatly alter APP processing, resulting in enhanced A-β 1-42 formation. Amyloid plaques are also detected in aged patients with Down's Syndrome who survive up to the age of 30. The observed up-regulation of APP expression in Down's Syndrome is probably a cause of the development of AD in Down's patients (Rumble et al., N. Engl. J. Med. 320:1446-52 (1989); Mann, Neurobiol. Aging 10: 397-399 (1989)). Amyloid plaques are also present in the normal aging brain, although at a lower number (Vickers et al., Exp. Neurol. 141:1-11 (1996)).

The different forms of human APP presently known range in size from 695-770 amino acids, localize to the cell surface, and have a single C-terminal transmembrane domain. A number of APP cDNA's have been identified, including the three most abundant forms, APP695 described by Kang et al. (1987) Nature 325: 733-736 which is designated as the "normal" APP; the 751 amino acid polypeptide (APP751) described by Tanzi et al. (1988) Nature 331: 528-530; and the 770 amino acid polypeptide (APP770) described by Kitaguchi et. al. (1988) Nature 331: 530-532. These forms arise from a single precursor RNA by alternative splicing. The A-β peptide, which is common to each of the three splice variants of APP, is derived from a region of APP adjacent to and containing a portion of the transmembrane domain.

Three different proteases process APP in vivo (Vassar and Citron, Neuron 27: 419-422 (2000)). Alpha-secretase cleaves APP 12 amino acid residues from the lumenal surface of the plasma membrane; it is not involved in A-β production. The first step of Aβ generation is performed by cleavage of APP by β-secretase (BACE), a type I membrane-bound aspartyl protease. BACE cleavage generates a 100-kDa soluble form (sAPP) of the ectodomain—the portion of APP that projects from the cell surface—and a 12-kDa membrane-associated intermediate peptide of 99 amino acids (termed C99) containing the N-terminus of the AB peptide (Vassar et al., Science 286(5440):735-41 (1999). The C99 peptide is then processed by the protease gamma-secretase to yield various Aβ peptides differing in size or terminal modification (40-42 and 43 amino acid residues being the most frequent peptides found in vivo) (for review, see Selkoe et al., Nature 399(6738 Suppl):A23-31 (1999); Tekirian, J. Alzheimers. Dis. 3(2):241-248. (2001)). The APP sequence near the β-secretase cleavage site is:

EVKM*DAE. (SEQ ID NO: 34)

These residues are labeled P4-P3-P2-P1*P1'-P2'-P3' in standard protease nomenclature with the cleavage site between P1 and P1' marked by *. Mutations in this region, such as the KM to NL mutation (the so-called Swedish mutation), can transform APP into a more preferred substrate for BACE. Hence, amino acid sequence changes in APP that result in increased APP cleavage by BACE increase the likelihood of the development of Alzheimer's (Citron et al., Nature 360(6405): 672-674 (1992)). Experimental evidence suggests that APP processing is sequential and that cleavage of APP by beta-secretase is a prerequisite for gamma-secretase-mediated APP processing. Cleavage within the transmembrane region of APP by gamma-secretase results in the 40/42-residue Aβ peptide, whose elevated production and accumulation in the brain are the central events in the pathogenesis of Alzheimer's disease (Selkoe,. Nature 399:23-31 (1999)). In addition, it is now clear that BACE can again cut Aβ peptide 40-42 after gamma-secretase to generate a neurotoxic Aβ34 peptide, at the expense of Abeta40-42 (Fluhrer et al., J. Biol. Chem. 278(8): 5531-5538 (2003)).

Many of the existing therapeutic strategies for AD have focused on gamma-secretase inhibition. However, it now appears that such strategies may not be sufficient, or even sound, to treat or prevent AD. For example, it is now clear that the C99 peptide itself, which requires BACE and not gamma-secretase cleavage for generation, includes the entire Aβ peptide, and is neurotoxic when evaluated in cultured cells, also accumulates in the AD brain (Tekirian, J. Alzheimers. Dis. 3(2):241-248. (2001)). Furthermore, gamma-secretase inhibitors have been shown to seriously affect the immune system and result in the accumulation of C terminal APP fragments, which are themselves toxic. In addition, gamma-secretase inhibition may alter the processing of various vital proteins (Doerfler, et al., Proc. Natl. Acad. Sci. USA 98 :9312-9317 (2001), Ni et al., Science 294: 2179-2181 (2001), Marambaud, et al., EMBO J. 21: 1948-1956 (2002), Kim, et al., J. Biol. Chem. 277: 499976-499981 (2002)). While a lack of BACE activity is not inevitably fatal in utero, a double-genetic knock-out of the presenilin 1 and 2 genes did prove to be so (Herreman, et al. Proc. Natl. Acad. Sci. USA 96: 11872-11877 (1999)). This toxicity is primarily a result of inhibition of Notch signaling pathway, which is involved in cell-to-cell signaling. Indeed, the Notch receptor and its cognate ligands Jagged and Delta are known substrates of presenilins (De Strooper, et al. Nature 398: 518-522 (1999)) and because the cleavage of Notch and its ligands leads to the release of proteolytic fragments active in cell signaling (LaVoie and Selkoe, J. Biol. Chem. 278(36): 34427-34437 (2003)).

In contrast, the in-vivo processing of the β-secretase site of the APP peptide is thought to be the rate-limiting step in Aβ peptide production (Sinha, S. & Lieberburg, Proc Natl Acad Sci USA. 96(20):11049-53 (1999); Vassar, Adv. Drug Deliv. Rev. 54(12):1589-1602 (2002)). BACE does not appear to participate in the generation of other physiologically important proteins (Cai et al., Nat. Neurosci 4: 233-234 (2001); Luo et al., Nat. Neurosci 4: 231-232 (2001)). Therefore, BACE appears as the strongest therapeutic target for decreasing or inhibiting Aβ generation.

BACE is synthesized as an inactive pro-enzyme. During maturation in the secretory pathway, BACE undergoes glycosylation at 3 of 4 N-linked sites and is separated from its propeptide domain by a member of the proprotein convertase family of proteases. In addition, BACE also undergoes palmitoylation at cysteine residues within its cytoplasmic domain and is phosphorylated at its C terminus. After core glycosylation in the endoplasmic reticulum (ER), BACE is rapidly and efficiently transported to the Golgi apparatus before targeting to the endosomal system (Fluhrer, R. et al.; J Biol. Chem. 278(8):5531-5538 (2003)).

To date, three isoforms of BACE have been isolated: BACE476, BACE457 and BACE432. All of these isoforms are in-frame deletions generated by the alternative usage of the exon3 region of the gene, and all of them exhibit much less APP processing activity, if any at all, than BACE501 (Bodendorf, et al., J. Biol. Chem. 276(15):12019-12023 (2001), Zohar et al., Brain Res. Mol. Brain. Res. 115(1):63-68 (2003), Tanahashi and Tabira, Neurosci. Lett. 307(1):9-12 (2001)).

SUMMARY OF THE INVENTION

The present invention is drawn to compositions and methods related to the identification of a new isoform of human beta-secretase (BACE), which is selectively expressed by brain tissue from patients suffering from a neuropathological condition (e.g., the human AD brain), which is catalytically active and which is pharmacologically different from the existing other active native BACE isoform BACE501. This new neuropathological-specific isoform of BACE, termed BACE455, has been discovered to result from the deletion of exon 4 and the development of a novel nucleotide and corresponding amino acid sequence present in the junction of exon3 and exon5.

Based on the published crystal structure of native BACE, it is anticipated that the novel isoform BACE455 of the present invention has a similar 3D structure to BACE, with the two aspartate residues within the active site of the protease still facing each other. However, the active site of BACE455 is more open and accessible and is therefore likely to produce significantly increased levels of Aβ peptide as compared to the native BACE molecule. In addition, BACE455 lacks an endoproteolytic site that is responsible for BACE inactivation and thus activity regulation in the native molecule. Therefore, compared to BACE and other known BACE isoforms, BACE455 lacks posttranslational regulation, has an altered 3-D structure, and is likely to produce increased levels of pathological Aβ peptide. BACE455 is significantly different from BACE501 in terms of inhibitory profile. This is shown using a well described inhibitor. Thus, the deletion of exon4 in BACE455 generates a significant pharmacological difference when compared to other known active BACE isoforms.

It is postulated that the observed functional and pharmacological properties of this isoform which distinguish it from native BACE may contribute to and selectively drive pathological conditions in mammals, particularly in human subjects.

Isolated BACE455, as well as distinctive fragments thereof, and corresponding nucleic acids can be used for the diagnosis of neuropathological conditions which are associated with BACE455 and for the screening of drugs, especially inhibitors of BACE455, which are therapeutically active in the treatment of neurological disorders, particularly neuropathological conditions including neurodegenerative disorders and dementia, more preferably disorders now known to be related to Aβ formation or accumulation such as Alzheimer's disease and related disorders.

In another embodiment of the invention are provided methods for the treatment of neuropathological conditions comprising the administration to affected tissue of an inhibitor of BACE455 transcription, translation, or activity.

By a "neuropathological condition" is meant one or more conditions including, but not limited to, Motor Neuron Disease (ALS), Down's syndrome, Parkinsonian Syndromes, multiple sclerosis, diffuse cerebral cortical atrophy, Lewy-body dementia, Pick disease, mesolimbocortical dementia, thalamic degeneration, bulbar palsy, Huntington chorea, cortical-striatal-spinal degeneration, cortical-basal ganglionic degeneration, cerebrocerebellar degeneration, familial dementia with spastic paraparesis, polyglucosan body disease, Shy-Drager syndrome, olivopontocerebellar atrophy, progressive supranuclear palsy, dystonia musculorum deformans, Hallervorden-Spatz disease, Meige syndrome, familial tremors, Gilles de la Tourette syndrome, acanthocytic chorea, Friedreich ataxia, Holmes familial cortical cerebellar atrophy, AIDS related dementia, Gerstmann-Straussler-Scheinker disease, progressive spinal muscular atrophy, progressive balbar palsy, maculopathies and retinal degeneration, such as Non-Exudative Age Related Macular Degeneration (ARMD), Exudative Age Related Macular Degeneration, primary lateral sclerosis, hereditary muscular atrophy, spastic paraplegia, peroneal muscular atrophy, hypertrophic interstitial polyneuropathy, heredopathia atactica polyneuritiformis, optic neuropathy, diabetic retinopathy, Alzheimer's disease and opthalmoplegia. Examples of ocular conditions include, but are not limited to, glaucoma, including open angle glaucoma, ocular hypertension, maculopathies and retinal degeneration, such as Non-Exudative Age Related Macular Degeneration (ARMD), Exudative Age Related Macular Degeneration (ARMD), Choroidal Neovascularization, Diabetic Retinopathy, Central Serous Chorioretinopathy, Cystoid Macular Edema, Diabetic Macular Edema, Myopic Retinal Degeneration; inflammatory diseases, such as Acute Multifocal Placoid Pigment Epitheliopathy, Behcet's Disease, Birdshot Retinochoroidopathy, Infectious (Syphilis, Lyme, Tuberculosis, Toxoplasmosis), Intermediate Uveitis (Pars Planitis), Multifocal Choroiditis, Multiple Evanescent White Dot Syndrome (MEWDS), Ocular Sarcoidosis, Posterior Scleritis, Serpiginous Choroiditis, Subretinal Fibrosis and Uveitis Syndrome, Vogt-Koyanagi-Harada Syndrome, Punctate Inner Choroidopathy, Acute Posterior Multifocal Placoid Pigment Epitheliopathy, Acute Retinal Pigement Epitheliitis, Acute Macular Neuroretinopathy; vascular and exudative diseases, such as Diabetic retinopathy, Central Retinal Arterial Occlusive Disease, Central Retinal Vein Occlusion, Disseminated Intravascular Coagulopathy, Branch Retinal Vein Occlusion, Hypertensive Fundus Changes, Ocular Ischemic Syndrome, Retinal Arterial Microaneurysms, Coat's Disease, Parafoveal Telangiectasis, Hemi-Retinal Vein Occlusion, Papillophlebitis, Central Retinal Artery Occlusion, Branch Retinal Artery Occlusion, Carotid Artery Disease (CAD), Frosted Branch Angiitis, Sickle Cell Retinopathy and other Hemoglobinopathies, Angioid Streaks, Familial Exudative Vitreoretinopathy; Eales Disease; traumatic, surgical and environmental disorders, such as Sympathetic Ophthalmia, Uveitic Retinal Disease, Retinal Detachment, Trauma, Retinal Laser, Photodynamic therapy, Photocoagulation, Hypoperfusion During Surgery, Radiation Retinopathy, Bone Marrow Transplant Retinopathy; proliferative disorders, such as Proliferative Vitreal Retinopathy and Epiretinal Membranes; infectious disorders, such as Ocular Histoplasmosis, Ocular Toxocariasis, Presumed Ocular Histoplasmosis Syndrome (POHS), Endophthalmitis, Toxoplasmosis, Retinal Diseases Associated with HIV Infection, Choroidal Disease Associate with HIV Infection, Uveitic Disease Associate with HIV Infection, Viral Retinitis, Acute Retinal Necrosis, Progressive Outer Retinal Necrosis, Fungal Retinal Diseases, Ocular Syphilis, Ocular Tuberculosis, Diffuse Unilateral Subacute Neuroretinitis, Myiasis; genetic disorders, such as Retinitis Pigmentosa, Systemic Disorders with Accosiated Retinal Dystrophies, Congenital Stationary Night Blindness, Cone Dystrophies, Stargardt's Disease And Fundus Flavimaculatus, Best's Disease, Pattern Dystrophy of the Retinal Pigmented Epithelium, X-Linked Retinoschisis, Sorsby's Fundus Dystrophy, Benign Concentric Maculopathy, Bietti's Crystalline Dystrophy, pseudoxanthoma elasticum; retinal injuries, such as Macular Hole, Giant Retinal Tear; retinal tumors, such as Retinal Disease Associated With Tumors, Congenital Hypertrophy Of The RPE, Posterior Uveal Melanoma, Choroidal Hemangioma, Choroidal Osteoma, Choroidal Metastasis, Combined Hamartoma of the Retina and Retinal Pigmented Epithelium, Retinoblastoma, Vasoproliferative Tumors of the Ocular Fundus, Retinal Astrocytoma, and Intraocular Lymphoid Tumors.

By "isolated" is meant a molecule existing in an environment other than that normally present in nature without human intervention. Thus, for example, "isolated BACE455" includes naturally-produced BACE455 contained in a cell lysate, purified or partially purified BACE455, recombinant BACE455, as well as BACE455 existing within a heterologous host cell or culture, such as tissue culture cell from any organism (including, without limitation, human, rat, monkey or other mammalian cells, bacterial or fungal cells, or insect cells).

In one embodiment of this invention, methods are described which involve the selective inhibition of BACE455 protein activity. Such methods can be used therapeutically to inhibit the progression of neuropathological conditions such as, without limitation, Alzheimer's disease, other dementia, glaucoma, Parkinson's disease, ALS, and the effects of stroke.

In another embodiment, this invention is drawn to the use of BACE455 mRNA encoding BACE455 or a distinctive fragment thereof, BACE455 protein, or any distinctive fragment of the BACE455 protein, to screen for molecules that inhibit the production of Aβ peptide.

Preferably a fragment of a protein or polypeptide in accordance with the present invention comprises at least 10 amino acids comprising a contiguous amino acid sequence, more preferably at least 9 amino acids comprising a contiguous amino acid sequence, even more preferably at least 8 amino acids comprising a contiguous amino acid sequence, even more preferably at least 7 amino acids comprising a contiguous amino acid sequence, even more preferably at least 6 amino acids comprising a contiguous amino acid sequence, even more preferably at least 5 amino acids comprising a contiguous amino acid sequence.

Preferably a fragment of a nucleic acid or polynucleotide in accordance with the present invention comprises at least 30 nucleotides comprising a contiguous nucleotide sequence, more preferably at least 27 nucleotides comprising a contiguous nucleotide sequence, even more preferably at least 24 nucleotides comprising a contiguous nucleotide sequence, even more preferably at least 21 nucleotides comprising a contiguous nucleotide sequence, even more preferably at least 18 nucleotides comprising a contiguous nucleotide sequence, even more preferably at least 15 nucleotides comprising a contiguous nucleotide sequence.

By "distinctive" when used to describe a nucleic acid encoding the BACE455 protein or a fragment thereof, is meant that the nucleotide sequence of such nucleic acid comprises at least one codon derived from exon 3 immediately proximal to at least one codon derived from exon 5 of the BACE 455 DNA sequence, encodes a protein or fragment thereof that has the same amino acid sequence encoded by such a nucleic acid or fragment, or is exactly complementary to such nucleotide sequence. In a particular embodiment, a distinctive nucleic acid comprises a nucleotide sequence comprising at least 5 contiguous nucleotides present in the junction of exon3 and exon5 of BACE455.

By "distinctive" when used to describe the BACE455 protein or a fragment thereof, is meant a peptide, polypeptide or protein comprising an amino acid sequence encoded by a distinctive nucleic acid encoding the BACE455 protein or a fragment thereof.

The BACE455 protein, distinctive fragments thereof and nucleic acids encoding these molecules can be used by those skilled in the art to design new BACE455 inhibitors, using commercially available software programs and techniques familiar to those in organic chemistry and enzymology. Such inhibitors are both useful in the diagnosis and treatment and/or prevention of Alzheimer's disease and other neuropathological conditions. Methods for making BACE455 inhibitors may make use of techniques well known in the art, such as, without limitation, combinatorial and other chemical libraries, use of the isolated BACE455 protein or a distinctive fragment thereof in high throughput screening of chemical libraries, rational drug design using medicinal chemistry techniques based on structure-activity relationships, and the like. Polypeptides of the present invention may be employed in conventional low capacity screening methods and also in high-throughput screening (HTS) formats. Such HTS formats include, for example, 96- and, and 384-well microtiter plates (see Bennett, et al., J. Mol. Recognition, 8:52-58 (1995); and Johanson, et al., J. Biol. Chem., 270(16): 9459-9471 (1995)). Exemplary methods that can be used for making BACE inhibitors have been disclosed in WO 9967221, WO 9967220, WO 9967219, WO 9966934, WO 9932453, WO 9838177, WO 9828268, WO 9822494, WO 9822493, WO 9822441, WO 9822433, and WO 9822430. Methods for making combinatorial libraries of compounds are disclosed in references such as Turner et al., Biochemestry 40: 10001-10006 (2001) or Gruninger-Leicht et al., J. Biol. Chem. 277: 4687-4693 (2002).

BACE455 inhibitors may be chosen from small molecule inhibitors, peptides, antisense oligonucleotides, iRNA, and blocking antibodies. Thus, inhibition of BACE455 includes the use of agents which inhibit BACE455 transcription, splicing, translation, and/or activity in vivo.

The present invention is preferably, though not exclusively, drawn to BACE455 inhibitors that alternatively exhibit 2-fold, or 5-fold, or 10-fold, or 30-fold, or 100-fold, or 1000 fold, or >1000 fold selectivity in the inhibition of BACE455 as compared to the other known BACE isoforms. Such inhibitors have an improved utility, compared to compounds that lack such selectivity, or which preferably inhibit native BACE rather than BACE455. Selective BACE455 inhibitors having a 2-fold, 5-fold, 10-fold or greater selectivity at inhibiting BACE455 have a number of benefits including greater efficacy at inhibiting pathological disease progression, decreased side effects due to less inhibition of non-pathological Aβ production, and improved safety due to the increased selectivity of such compounds.

The BACE455 protein, nucleic acid, distinctive fragments of these molecules, and BACE455 inhibitors can be used for the purpose of diagnosis of neuropathological conditions. Compounds specifically binding to BACE455 polypeptide or nucleic acid, or to a distinctive fragment thereof, can help identify individuals prone to develop AD. Additionally, BACE455 inhibitors can be used with therapeutic effect for treatment and/or prevention of Alzheimer's disease and conditions associated with elevated levels of Aβ 40 or 42 peptide, and the accumulation of the peptide in amyloid plaques, as well as other neuropathological conditions.

In another aspect of this invention, the novel deletion of exon 4 and the novel junction of exons 3 and 5 may be used to diagnose and/or assess the actual or potential development of a neuropathological condition. For example, through the development of in vitro nucleic acid- and/or antibody-based assays, including quantitative assays, of human tissue or fluids, one can determine whether the patient suffers from, or is inclined to suffer from, neuropathological conditions that involve the production and expression of BACE455. Such assay methods may involve, without limitation, nucleic acid detection by, for example, Northern Blot, oligonucleotide-based junction array; nucleic acid amplification methods such as RT-PCR, quantitative PCR and ligation-PCR and other methods. These methods may include the use of an oligonucleotide probe capable of selectively or specifically detecting the region of the analyte comprising the new splice junction. BACE455 may also be directly detected using specific ligands thereof, for example, an antibody specifically recognizing the region of BACE455 comprising the new splice junction, as one example, the region comprising amino acid residues 190 to 235 of the BACE455 protein.

In yet another embodiment, the present invention includes bacterial, insect and mammalian cells or cell lines and transgenic non-human animals that specifically express the BACE455 isoform or a distinctive fragment thereof, in preference to the native BACE501 or other isoforms. Preferred host cells are mammalian cells. Non limiting examples of suitable mammalian cells include the NIH3T3 line of mouse embryo cultures (Jainchill et al. J. Virol. 4: 549-553 (1969)), Chinese hamster ovary cells (CHO), human embryonic kidney cell line 293 or neuroblastoma cell line SH-SY5Y cell line (Biedler et al. Cancer Res. 38: 3751-3757 (1978)). For example, cell lines specifically expressing the BACE455 isoform can be obtained by (a) transfecting a BACE455 expression vector, such as, for example, a pcDNA3 vector with BACE455 full length cDNA cloned into the expression cassette, into the cell type of interest and (b) selecting transfected cells using antibiotics or selection agents corresponding to the resistance gene encoded by the expression vector. Methods for the generation of clonal cell lines composed by stable transformant are disclosed, for example, in Wigler et al. (Cell 11: 223-232 (1977)); Kriegler (Gene Transfer and Expression. Stockton Press, New York, N.Y. (1990)) or Gramer & Goochee (Biotechnol. Prog. 9(4):366-73 (1993)). Alternatively, transfected cells can be used in transient transfection assays to monitor BACE455 activity without further selection. Transgenic animals may be obtained, as known in the art, by recombination techniques using methods well known in the art of molecular biology which are described in such reference as Sambrook et al. (Molecular Cloning: a Laboratory Manual, Cold Spring Harbor Press, Cold Spring Harbor N.Y. (1988)) and Ausubel (Current Protocols in Molecular Biology (1989)).

Such cell lines represent an original screening tool for compounds preventing Aβ processing, and non-human transgenic animals would be useful for studying the development of Aβ-dependent dementia and for identifying compounds that inhibit Aβ dependent disease progression in vivo.

BRIEF DESCRIPTION OF THE DRAWINGS

FIG. 1A: Nucleic acid sequence (SEQ ID NO: 1) of BACE455,

FIG. 1B: Amino acid sequence (SEQ ID NO: 2) of BACE455 and alignment of amino acid sequence with BACE501 (SEQ ID NO: 36).

FIG. 2: Immunolocalization on NIH 3T3 cells transfected with a construct expressing BACE455 or BACE501. Intracellular staining of BACE isoforms (BACE455, FIG. 2A: BACE501, FIG. 2B) on Triton X100-permeabilized cells using polyclonal anti-hBACE (481-501) (C-ter intracellular epitope). Extracellular staining of BACE isoforms (BACE455.

DETAILED DESCRIPTION OF THE INVENTION

Figures 2A, 2B, 2C, 2D:
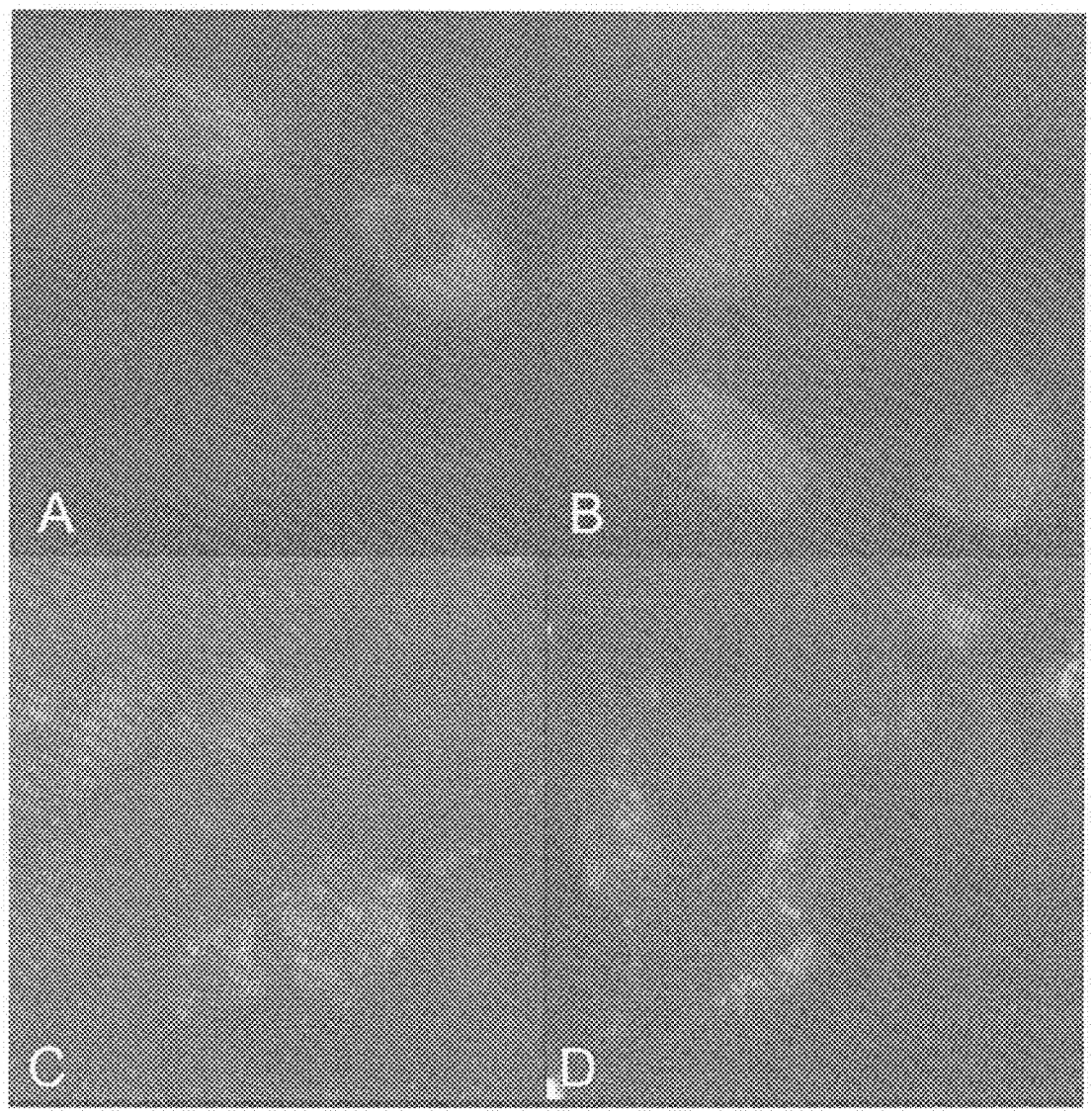
FIG. 2C; BACE501, FIG. 2D) on non-permeabilized cells using polyclonal anti-hBACE (46-65) (N-ter extracellular epitope). Photomicrograph showing that BACE455 presents similar intracellular localization than BACE501, is efficiently exported to the cellular membrane where it displays comparable extracellular membranous immunoreactivity to BACE501.

In a first embodiment, the present invention is drawn to a polypeptide comprising all or a distinctive fragment of the BACE455 polypeptide. The BACE455 amino acid sequence is depicted in FIG. 1. The term "BACE 455" or "BACE455 polypeptide" means any BACE polypeptide (preferably of human origin), that comprises a deletion of all or part of exon 4 of the gene encoding the wild-type BACE peptide.

Preferred examples of distinctive fragments of the BACE455 polypeptide are those comprising the amino acid sequence IARIIG (SEQ ID NO: 3). Further examples of such fragments are polypeptides comprising the amino acid sequence EIARIIG (SEQ ID NO: 4), typically a sequence selected from EIARIIGG (SEQ ID NO: 5), AEIARIIG (SEQ ID NO: 6), AEIARIIGG (SEQ ID NO: 7), AEIARIIGGI (SEQ ID NO: 8), YAEIARIIG (SEQ ID NO: 9), YAEIARIIGG (SEQ ID NO: 10) and YAEIARIIGGI (SEQ ID NO: 11). Most preferred fragments are at least 6, 7, 8, 9 or 10 amino acids long.

A polypeptide of the present invention comprising a distinctive BACE455 polypeptide fragment may comprise the entire amino acid sequence of BACE455 or a variant thereof. The term "variant" in this context designates any polypeptide comprising a distinctive fragment of the BACE455 polypeptide and further comprising a modified amino acid sequence as compared to the sequence depicted in FIG. 1 as a result of one or several amino acid mutation(s), substitution(s) and/or insertion(s). Typically, such BACE455 variants lack all of exon 4. Preferred variants are naturally-occurring variants, i.e., BACE polypeptides resulting from polymorphism, splicing, etc., which lack exon 4. Most preferred polypeptides of this invention are of human origin and/or retain one property of BACE455 of FIG. 1, in particular at least one BACE455-selective immunological property and/or a beta-secretase activity.

Such polypeptides may optionally comprise additional residues or functions, such as, without limitation, additional amino acid residues, chemical or biological groups, including labels, tags, stabilizer, targeting moieties, purification tags, secretory peptides, functionalizing reactive groups, etc. Such additional residues or functions may be chemically derivatized, added as an amino acid sequence region of a fusion protein, complexed with or otherwise either covalently or non-covalently attached. They may also contain natural or non-natural amino acids. The polypeptide may be in soluble form, or attached (or complexed with or embedded in) to a support, such as a matrix, a column, a bead, a membrane, a cell, a lipid or liposome, etc.

Certain polypeptides of the present invention may be used as such to cause production of Aβ peptide in vitro or in vivo. They may also be used to design specific reagents such as peptides, antibodies (and derivatives thereof), antagonists, agonists, etc. that specifically detect, bind or affect expression or activity of a BACE455 polypeptide as defined above. The polypeptides may also be used as immunogens in vaccine compositions or to produce or detect or dose specific antibodies.

In yet another embodiment, the present invention comprises a polynucleotide comprising a nucleotide sequence encoding a BACE455 polypeptide as defined above, including a distinctive fragment thereof. The polynucleotide preferably encodes a polypeptide that comprises a fragment of mammalian memapsin 2 (BACE) protein, wherein said polypeptide lacks all of exon4 (encoded by amino acids 190 to 235 of full-length BACE protein). A typical example of such a polypeptide comprises all or a distinctive fragment of the nucleotide sequence set forth in FIG. 1 (SEQ ID NO: 2).

A particular embodiment of this invention also includes any polynucleotide comprising a nucleotide sequence that selectively hybridizes to a distinctive fragment of BACE 455 RNA (or its exact complement) under stringent conditions. More preferably, such selectively hybridizing polynucleotide encodes a polypeptide having beta-secretase activity. By stringent conditions is intended, for example, incubations of hybridization filters at about 42° C. for about 2.5 hours in 2×SSC/0.1% SDS, followed by washing of the filters four times of 15 minutes in 1×SSC/0.1% SDS at 65° C. Protocols used are described in such reference as Sambrook et al. (Molecular Cloning: a Laboratory Manual, Cold Spring Harbor Press, Cold Spring Harbor N.Y. (1988)) and Ausubel (Current Protocols in Molecular Biology (1989)).

In a particularly preferred embodiment, the encoded BACE polypeptide comprises a distinctive fragment of a human BACE protein.

The nucleic acids, oligonucleotides and polynucleotides of the present invention may be DNA or RNA, such as genomic DNA, complementary DNA, synthetic DNA, mRNA, or analogs of these containing, for example, modified nucleotides such as 3' alkoxyribonucleotides, methylphosphanates, and the like, and peptide nucleic acids (PNAs), etc. The polynucleotide may be produced according to techniques well-known per se in the art, such as by chemical synthetic methods, in vitro transcription, or through recombinant DNA methodologies, using sequence information contained in the present application. In particular, the polynucleotide may be produced by chemical oligonucleotide synthesis, library screening, amplification, ligation, recombinant techniques, and combination(s) thereof.

A specific embodiment of this invention resides in a polynucleotide encoding a polypeptide comprising a distinctive fragment of BACE having the amino acid sequence set forth as SEQ ID NO 2.

Polynucleotides of this invention may comprise additional nucleotide sequences, such as regulatory regions, i.e., promoters, enhancers, silencers, terminators, and the like that can be used to cause or regulate expression of a BACE455 polypeptide.

Polynucleotides of this invention may be used to produce a recombinant polypeptide of this invention. They may also be used to design specific reagents such as primers, probes or antisense molecules (including antisense RNA, iRNA, aptamers, ribozymes, etc.), that specifically detect, bind or affect expression of a polynucleotide encoding a BACE455 polypeptide as defined above. They may also be used as therapeutic molecules (e.g., as part of an engineered virus, such as, without limitation, an engineered adenovirus or adeno-associated virus vector in gene therapy programs) or to generate recombinant cells or genetically modified non-human animals, which are useful, for instance, in screening compound libraries for agents that modulate the activity of BACE455.

A further aspect of this invention resides in a vector, such as an expression or reporter vector comprising a BACE455 polynucleotide as defined above. Such vectors may be selected from plasmids, recombinant viruses, phages, episomes, artificial chromosomes, and the like. Many such vectors are commercially available and may be produced according to recombinant techniques well known in the art, such as the methods set forth in manuals such as Sambrook et al., *Molecular Cloning* (2d ed. Cold Spring Harbor Press 1989), which is hereby incorporated by reference herein in its entirety.

A further aspect of this invention resides in a host cell transformed or transfected with a polynucleotide or a vector as defined above. The host cell may be any cell that can be genetically modified and, preferably, cultivated. The cell can be eukaryotic or prokaryotic, such as a mammalian cell, an insect cell, a plant cell, a yeast, a fungus, a bacterial cell, etc. Typical examples include mammalian primary or established cells (3T3, CHO, Vero, Hela, etc.), as well as yeast cells (e.g., *Saccharomyces* species, *Kluyveromyces*, etc.) and bacteria (e.g., *E. Coli*). It should be understood that the invention is not limited with respect to any particular cell type, and can be applied to all kinds of cells, following common general knowledge.

Nucleic Acid Probes

A specific type of polynucleotide of this invention is a nucleic acid probe that selectively hybridizes under stringent hybridization condition to a nucleic acid or fragment thereof encoding a distinctive fragment of the BACE455 polypeptide . . . . As is well-known in the art, "stringent hybridization conditions" depend upon the length of the probe and the ratio of guanine-cytosine pairs to thymine (uracil)-adenine pairs in the resulting hybrid.

Within the context of this invention, a "probe" refers to a nucleic acid or oligonucleotide having a polynucleotide sequence which is capable of selective hybridization with a distinctive fragment of BACE455 RNA (or the nucleotide sequence exactly complementary thereto), and which is suitable for detecting the presence of a BACE455 RNA (or nucleic acid having its exact complementary nucleic acid sequence) in any sample containing said RNA or complement. Probes are preferably perfectly complementary to a distinctive fragment of the BACE455 RNA. Probes typically comprise single-stranded nucleic acids of between 8 to 1400 nucleotides in length, for instance of between 10 and 1000, more preferably of between 15 and 800, typically of between 20 and 600. It should be understood that longer probes may be used as well. A preferred probe of this invention is a single stranded nucleic acid molecule of between 8 to 600 nucleotides in length, which can specifically hybridize to a distinctive fragment of BACE455 RNA.

A specific embodiment of this invention is a nucleic acid probe selective for an isoform of BACE which lacks exon 4, a nucleic acid probe that selective hybridizes to said isoform gene or RNA and does not substantially hybridize to at least one other BACE isoform containing a full length exon 4, and nucleic acid probes exactly complementary to these.

A further specific embodiment of this invention is a nucleic acid probe selective for BACE455 RNA, i.e., a nucleic acid probe that selectively hybridizes to said BACE455 gene or RNA and does not substantially hybridize to at least one other BACE isoform, and nucleic acids exactly complementary to these.

Selectivity, when used to denote nucleic acid hybridization, indicates that a probe is able to hybridization to the target sequence without substantially hybridizing to at least one other BACE-encoding nucleic acid.

Preferred probes of this invention comprise a sequence which is complementary to a distinctive fragment of the BACE455 RNA (or its exact complement). Specific examples of such probes comprise the nucleic acid sequence:

ATTGCCAGGATCATTGGA    SEQ ID NO: 12

The sequence of the probes can be derived from the sequences of the BACE455 RNA as provided in the present application. Nucleotide substitutions may be performed, as well as chemical modifications of the probe. Such chemical modifications may be accomplished to increase the stability of hybrids (e.g., intercalating groups or modified nucleotides, such as 2' alkoxyribonucleotides) or to label the probe, as disclosed above. Typical examples of labels include, without limitation, radioactivity, fluorescence, luminescence, enzymatic labelling, and the like. The probe may be hybridized to the target nucleic acid in solution, suspension, or attached to a solid support, such as, without limitation, a bead, column, plate, substrate (to produce nucleic acid arrays or chips).

In one example, a BACE455-selective oligonucleotide probe of 15 by exactly complementary to a distinctive fragment of the BACE455 RNA is labeled with a chemiluminescent compound such as an N-hydroxysuccinimide (NHS) ester of acridinium (e.g., 4-(2-succinimidyloxycarbonyl ethyl) phenyl-10-methylacridinium 9-carboxylate fluorosulfonate) generally as described in Weeks et al., Clin. Chem. 29: 1474-1478 (1983), and Nelson et al., U.S. Pat. No. 5,658,737, both of which are hereby incorporated by reference herein. Reaction of the primary amine of the linker arm:hybridization probe conjugate with the selected NHS-acridinium ester is performed as follows. The oligonucleotide hybridization probe:linker arm conjugate synthesized as described above is vacuum-dried in a Savant SPEED-VAC® drying apparatus, then dissolved in 8 µl of 0.125 M HEPES buffer (pH 8.0) in 50% (v/v) DMSO. To this solution is added 2 µl of 25 mM of the desired NHS-acridinium ester. The solution is mixed and incubated at 37° C. for 20 minutes.

An additional 3 µl of 25 mM NHS-acridinium ester in DMSO is added to the solution and mixed gently, then 2 µl of 0.1 M HEPES buffer (pH 8.0) is added, mixed, and the tube is allowed to incubate for an additional 20 minutes at 37° C. The reaction is quenched with the addition of 5 µl 0.125 M lysine in 0.1 M HEPES buffer (pH 8.0) in DMSO, which is mixed gently into the solution.

The labeled oligonucleotide is recovered from solution by the addition of 30 µl 3 M sodium acetate buffer (pH 5.0), 245 µl water, and 5 µl of 40 mg/ml glycogen. Six hundred forty microliters of chilled 100% ethanol is added to the tube, and the tube is held on dry ice for 5 to 10 minutes. The precipitated labeled probe is sedimented in a refrigerated microcentrifuge at 15,000 rpm using a standard rotor head. The supernatant is aspirated off, and the pellet is redissolved in 20 µl 0.1 M sodium acetate (pH 5.0) containing 0.1% (w/v) sodium dodecyl sulfate (SDS).

Eleven fmoles of the labeled probe is hybridized to various amounts (0.00, 0.01, 0.02, 0.05, 0.20, 0.50, 2, 5, 20, 50, 200, 500, 2000, and 5000 fmoles) of the target BACE455 RNA. Each set consisted of 100 µl hybridization reactions containing 100 mM lithium succinate (pH 5.0), 8.5% (w/v) lithium lauryl sulfate, 1.5 mM EDTA, and 1.5 mM EGTA and each reaction mixture was incubated at 50.degree. C. for 50 minutes. Three hundred microliters of a solution containing 150 mM Na$_2$B$_4$O$_7$ (pH 8.6) and 1% (v/v) TRITON®. X-100 were added to each reaction, and the mixtures incubated at 50° C. for 11 minutes. The reaction mixtures were then placed into a LEADER® 50 luminometer (Gen-Probe, Inc.), and a chemiluminescent reaction initiated in each mixture upon the injection of 200 µl 0.1% (v/v) H$_2$O$_2$ and 1 mM HNO$_3$, followed by 200 µl of 1.5 N NaOH. Chemiluminescence was read at a wavelength range from 300 to 650 nm for 2 seconds following the second injection and compared to a negative and positive control standard. Significant chemiluminescence above the negative control indicates the presence of a BACE455-selective hybrid.

Nucleic Acid Primers

Other selective polynucleotides of this invention are nucleic acid primers for amplifying a region comprising a distinctive fragment of a BACE455 RNA or its exact complement. Such primers are designed to amplify BACE455-selective nucleic acid fragments.

Particular primers of this invention are able to selectively hybridise with a portion of a BACE455 RNA or its exact complement that flanks an isoform-specific nucleic acid sequence region, more preferably a region of BACE455 RNA resulting from the newly created junction between exon 3 and exon 5., or its exact complement. The term "flanks" indicates that the portion should be located at a distance of the target region that is compatible with conventional polymerase activities, e.g., not above 300 by from the newly created junction, preferably not exceeding 200, 150, 100 or, further preferably, 50 by upstream from said junction. Examples of such primers comprise or are complementary to a portion of the sequences flanking nucleotide region 567-704 in SEQ ID NO: 1. Specific examples of such primers comprise the following sequences: AGGCATCCTG (SEQ ID NO: 13), GGGCTGGCCT (SEQ ID NO: 14), ATGCTGAGAT (SEQ ID NO: 15), TGCCAG (SEQ ID NO: 16), GATCAT (SEQ ID NO: 17), TGGAGGTATC (SEQ ID NO: 18), GACCACTCGC (SEQ ID NO: 19), TGTACACAGG (SEQ ID NO: 20) or CAGTCTCTGG (SEQ ID NO: 21).

Other particular primers of this invention are able to selectively hybridise with an isoform-specific region comprising a distinctive fragment of BACE455 RNA or its exact complement, more specifically a region of BACE455 resulting from a newly created junction between exon 3 and exon 5. Such primers are advantageous in that amplification occurs only when the template comprises the isoform-specific alteration. By using such primers, the detection of an amplification product indicates the presence of BACE455 RNA. In contrast, the absence of amplification product indicates that the specific alteration is not present in the sample. Examples of such primers comprise all or a portion of the following sequences:

| | |
|---|---|
| CAGGAT, | (SEQ ID NO: 22) |
| CCAGGATC, | (SEQ ID NO: 23) |
| GCCAGGATCA or | (SEQ ID NO: 24) |
| ATTGCCAGGATCATTGGA. | (SEQ ID NO: 25) |

A further aspect of this invention also includes at least one pair of nucleic acid primers, wherein said pair of primers comprise a sense and a reverse primer, and wherein said sense and reverse primer allows selective amplification of the BACE455 RNA or an isoform-specific portion thereof, or the exactly complementary sequence. A further embodiment of this invention is a pair of nucleic acid primers, wherein said pair comprises a sense and a reverse primer, and wherein said sense and reverse primers allow selective amplification of all or an isoform-specific portion of a BACE RNA isoform lacking all or part of exon4.

Typical primers of this invention are single-stranded nucleic acid molecules of about 5 to 60 nucleotides in length, more preferably of about 8 to about 35 nucleotides in length, further preferably of about 10 to 25 nucleotides in length. Their sequences can be derived or inferred directly from the nucleotide sequence of BACE455 as disclosed in this application. Perfect complementarity is preferred, to ensure high specificity. However, certain mismatch may be tolerated.

Inhibitory Nucleic Acids

The invention also relates to nucleic acid molecules that can specifically alter expression or activity of a BACE455 polypeptide or polypeptide comprising a fragment thereof (or of any BACE polypeptide lacking a functional exon4). Such inhibitory nucleic acids include antisense nucleic acids, iRNA, ribozymes, aptamers, and the like. These inhibitory nucleic acids comprise a sequence that is complementary to a portion of the target isoform gene or RNA, and cause a specific reduction in transcription or translation thereof. Absolute complementarity, although preferred, is not required.

Techniques for the production and use of such molecules are well known to those of skill in the art, and are succinctly described below. Oligonucleotides may be synthesized by standard methods known in the art, e.g. by use of an automated DNA synthesizer (such as are commercially available from Applied Biosystems, Inc.). As examples, phosphorothioate oligonucleotides may be synthesized by the method of Matsukura et al. (Gene. 1988 72:343-7), etc.

Antisense deoxynucleotides have been widely used to study the effect of a given gene (for review, see Stein & Cheng, Science 261: 1004-12 (1993), and can be used on exon-exon junctions and target specific mRNA isoform (Sugi et al. Dev. Biol. 157: 28-37 (1993); Mahon et al. Exp Hematol. 23:1606-11 (1995); Desire et al. J. Neurochem. 75:151-163 (2000)).

Antisense oligonucleotides can be DNA or RNA or chimeric mixtures or derivatives or modified versions thereof, single-stranded or double-stranded. The oligonucleotide can be modified at the base moiety, sugar moiety, or phosphate backbone, for example, (selected from the group consisting of a phosphorothioate, a phosphorodithioate, a phosphoramidothioate, a phosphoramidate, a phosphordiamidate, a methylphosphonate, an alkyl phosphotriester, and a formacetal or analog thereof) to improve stability of the molecule, hybridization, etc. The oligonucleotide may include other appended groups such as peptides (e.g., for targeting host cell receptors in vivo), or agents facilitating transport across the cell membrane or the blood-brain barrier (Letsinger (1989) Proc. Natl. Acad. Sci. U.S.A. 86:6553-6556), hybridization-triggered cleavage agents (Krol (1988) Bio. Techniques 6:958-976) or intercalating agents (Zon (1988) Ann. N.Y. Acad. Sci. 616: 161-72 (1990)).

The antisense oligonucleotide can be an alpha.-anomeric oligonucleotide which forms specific double-stranded hybrids with complementary RNA in parallel strands (Gautier et al. (1987) Nucl. Acids Res. 15:6625-6641). The oligonucleotide is a 2'-O-methylribonucleotide (Mayeda et al. J. Biochem. 108: 399-405 (1990)), or a chimeric RNA-DNA analogue (Inoue et al. (1987) FEBS Lett. 215:327-330).

Gene silencing can also be achieved using small interfering RNAs in mammalian cells (Elbashir et al. Nature 411: 494-498; Brummelkamp et al. Science 296: 550-553 (2003) and has successfully been used in the alternative splicing context to study the functional relevance of specific isoforms (Celotto & Graveley, RNA 8: 718-724 (2002)).

Ribozymes are enzymatic RNA molecules capable of catalyzing the specific cleavage of RNA can also be used to prevent translation of target gene mRNA and, therefore, expression of target gene product (Sarver et al. (1990) Science 247:1222-1225; Rossi (1994) Current Biology 4:469-471). The mechanism of ribozyme action involves sequence specific hybridization of the ribozyme molecule to complementary target RNA, followed by an endonucleolytic cleavage event. Hammerhead ribozymes are modified ribozymes which cleave mRNAs at locations dictated by flanking regions that form complementary base pairs with the target mRNA. The construction and production of hammerhead ribozymes is well known in the art and is described more fully in Haseloff and Gerlach, 1988 (Nature) 334:585-591.

These inhibitory nucleic acids can be designed based on the sequences disclosed in the present application.

Specific Ligands

The invention also relates to ligands that selectively bind a BACE455 isoform or a distinctive fragment thereof, as disclosed above.

Different types of ligands may be contemplated, such as specific antibodies, synthetic molecules, aptamers, peptides, and the like.

In a specific embodiment, the ligand is an antibody, or a fragment or derivative thereof. Accordingly, a particular aspect of this invention resides in an antibody that specifically binds a BACE455-specific epitope, more preferably an epitope generated by the deletion of all or part of exon4 (encoded by amino acids 190 to 235 of SEQ ID NO 9).

Within the context of this invention, an antibody designates a polyclonal antibody, a monoclonal antibody, as well as fragments or derivatives thereof having substantially the same antigen specificity. Fragments include Fab, Fab'2, CDR regions, etc. Derivatives include single-chain antibodies, humanized antibodies, human antibodies, poly-functional antibodies, etc.

Antibodies against human BACE455 protein may be produced by procedures generally known in the art. For example, polyclonal antibodies may be produced by injecting the protein alone or coupled to a suitable protein into a non-human animal. After an appropriate period, the animal is bled, sera recovered and purified by techniques known in the art (see Paul, W. E. "Fundamental Immunology" Second Ed. Raven Press, NY, p. 176, 1989; Harlow et al "Antibodies: A laboratory Manual", CSH Press, 1988; Ward et al (Nature 341 (1989) 544). Monoclonal antibodies may be prepared, for example, by the Kohler-Millstein (2) technique (Kohler-Millstein, Galfre, G., and Milstein, C, Methods Enz. 73 p. 1 (1981)) involving fusion of an immune B-lymphocyte to myeloma cells. For example, antigen as described above can be injected into mice as described above until a polyclonal antibody response is detected in the mouse's serum. The mouse can be boosted again, its spleen removed and fusion with myeloma conducted according to a variety of methods. The individual surviving hybridoma cells are tested for the secretion of anti-BACE antibodies first by their ability to bind the immunizing antigen and then by their ability to immunoprecipitate BACE from cells.

An antibody "selective for a BACE455 polypeptide" designates an antibody that selectively binds a BACE455 polypeptide to a greater extent than other BACE isoforms, i.e., an antibody raised against a BACE455 polypeptide or an epitope-containing fragment thereof. Although non-specific binding towards other antigens may occur, binding to the target BACE455 polypeptide occurs with a higher affinity and can be reliably discriminated from non-specific binding. Preferred antibodies are selective for a BACE455 specific domain comprising the newly created junction region between exon 3 and exon 5. Antibodies selective for said domain allow the detection of the presence of BACE455 polypeptides in a sample. The ligand may be used in soluble form, or coated on a surface or support.

Specific examples of synthetic inhibitors include Gleevec and Brefeldin A. A specific example of a peptide inhibitor is BACE inhibitor III (SEQ ID NO: 3).

Detection and Diagnostics

The present invention allows the performance of detection or diagnostic assays that can be used, among other things, to detect the presence, absence, or amount of BACE455 or a corresponding nucleic acid in a sample or subject. The term "diagnostics" shall be construed as including methods of detecting the BACE455 isoform, corresponding nucleic acids, and fragments of these in mammalian (preferably human) samples, diagnostics (either qualitative and quantitative), pharmacogenomics, prognostic, and so forth.

In a particular aspect, the invention relates to a method of detecting a BACE455 nucleic acid or polypeptide, or fragments of these in a sample, preferably, a human tissue sample, comprising contacting said sample with a specific ligand thereof and determining the formation of a complex.

A particular object of this invention resides in a method of detecting the presence of or predisposition to a neurodegenerative disease or an associated disorder in a subject, the method comprising detecting the presence of a distinctive BACE455 nucleic acid or polypeptide in a sample from the subject, particularly a BACE isoform lacking all of exon4, even more preferably a BACE isoform having the polynucleotide or amino acid sequence SEQ ID NO: 1 or SEQ ID NO: 2, respectively.

Another embodiment of this invention is directed to a method of assessing the response of a subject to a treatment of a neurodegenerative disease or an associated disorder, the method comprising detecting the presence of a distinctive BACE455 nucleic acid or polypeptide in a sample from the subject at different times before and during the course of treatment.

This invention also relates to a method of determining the efficacy of a treatment of a neurodegenerative disease or an associated disorder, the method comprising (i) providing a tissue sample from the subject during or after said treatment, (ii) determining the presence and/or abundance of a BACE455 nucleic acid or polypeptide, or distinctive fragment thereof, in said sample and (iii) comparing said presence and/or abundance to the amount of such nucleic acid, polypeptide, or fragment in a reference sample from said subject taken prior to or at an earlier stage of the treatment.

The presence (or increase) in a distinctive BACE455 polypeptide or nucleic acid in a sample is indicative of the presence, predisposition or stage of progression of a neurodegenerative disease or related disorders. Therefore, the invention allows the design of appropriate therapeutic intervention, which is more effective and customized. Also, this determination at the pre-symptomatic level allows a preventive regimen to be applied.

Determination of the presence, absence, or relative abundance of a distinctive BACE455 polypeptide or nucleic acid in a sample can be performed by a variety of techniques. More preferably, the determination comprises contacting the sample with BACE 455-selective reagents such as probes, primers or ligands, as defined above, and thereby detecting the presence, or measuring the amount, of BACE455 polypeptide or nucleic acids originally in the sample. Contacting may be performed in any suitable device, such as a plate, microtiter dish, test tube, well, glass, column, and so forth In specific embodiments, the contacting is performed on a substrate coated with the reagent, such as a nucleic acid array or a specific ligand array. The substrate may be a solid or semi-solid substrate such as any suitable support comprising glass, plastic, nylon, paper, metal, polymers and the like. The substrate may be of various forms and sizes, such as a slide, a membrane, a bead, a column, a gel, etc. The contacting may be made under any condition suitable for a detectable complex, such as a nucleic acid hybrid or an antibody-antigen complex, to be formed between the reagent and the nucleic acids or polypeptides of the sample.

In a specific embodiment, the method comprises contacting a sample from the subject with (a support coated with) a BACE 455 selective antibody, as described above, and determining the presence of an immune complex. Various well-known methods for detecting an immune complex can be used, such as ELISA, radio-immunoassays (RIA), and so forth.

In another specific embodiment, the method comprises contacting a sample from the subject with (a support coated with) a BACE 455-selective nucleic acid probe, as described above, under appropriate conditions allowing hybridization to occur, and determining the presence of a hybrid.

In another specific embodiment, the method comprises contacting a sample from the subject with a nucleic acid primer as defined above, under conditions allowing nucleic acid amplification to occur, and determining the presence of an amplification product ("amplicon"). Amplification may be performed according to various techniques known per se in the art, such as, without limitation, by polymerase chain reaction (PCR), ligase chain reaction (LCR), transcription-mediated amplification (TMA), strand displacement amplification (SDA) and nucleic acid sequence based amplification (NASBA).

Suitable methods to detect nucleic acids in a sample include, without limitation, the following methods: allele-specific oligonucleotide (ASO), allele-specific amplification, Southern blot (for DNAs), Northern blot (for RNAs), single-stranded conformation analysis (SSCA), fluorescent in situ hybridization (FISH), gel migration, clamped denaturing gel electrophoresis, heteroduplex analysis, etc.

The diagnostic methods of the present invention can be performed in vitro, ex vivo or in vivo, preferably in vitro or ex vivo. The sample may be any biological sample derived from a subject, which contains nucleic acids or polypeptides, as appropriate. Examples of such samples include fluids, tissues, cell samples, organs, biopsies, etc. Most preferred samples are blood, plasma, saliva, urine, seminal fluid, and the like. Prenatal diagnosis may also be performed by testing fetal cells or placental cells, for instance, the sample may be collected according to conventional techniques and used directly for diagnosis or stored. The sample may be treated prior to performing the method, in order to render or improve availability of nucleic acids or polypeptides for testing. Treatments may include, for instance one or more of the following: cell lysis (e.g., mechanical, physical, chemical, etc.), centrifugation, extraction, column chromatography, and the like.

Therapeutics

In addition to cleaving APP-based substrates, recombinant human BACE also cleaves a substrate with the sequence LVNM/AEGD (SEQ ID NO: 35) (Lin et al. Proc Natl Acad Sci USA. 97(4):1456-1460 (2000)), a sequence which is the in vivo processing site sequence of human presenilins. Presenilin 1 and presenilin 2 are unstable proteins which are processed and subsequently stabilized by an unknown protease (Capell et al., J. Biol. Chem. 273, 3205 (1998); Thinakaran et at, Neurobiol. Dis. 4, 438 (1998)). It is known that presenilins control the formation of A-β peptide by cleavage of APP at the gamma-secretase site, but also the activity of BACE. Presenilins therefore enhance the progression of Alzheimer's disease. Thus, the processing of presenilins by BACE would enhance the production of A-β peptide and therefore, further stimulate the progress of Alzheimer's disease. Therefore, a BACE inhibitor would decrease the likelihood of developing or slow the progression of Alzheimer's disease by inhibiting APP cleavage at the beta-secretase site and/(or) by preventing the processing of presenilins, thus indirectly inhibiting APP cleavage at the gamma-secretase site.

A further object of this invention is a pharmaceutical composition comprising a BACE455 inhibitor, preferably a BACE455-selective inhibitor, and a pharmaceutically acceptable carrier or vehicle. In a specific embodiment, the invention relates to a pharmaceutical composition comprising (i) a specific ligand of BACE455 or a BACE455 inhibitory nucleic acid molecule as described above and (ii) a pharmaceutically acceptable carrier or vehicle.

The invention also relates to a method of treating or preventing neurodegenerative diseases or an associated disorder in a subject, the method comprising administering to said subject an effective amount of a BACE455-selective inhibitor.

Another embodiment of this invention resides in a method of treating or preventing production or accumulation of Aβ peptide in a subject, the method comprising administering to said subject an effective amount of a BACE455-selective inhibitor.

The invention also relates, generally, to the use of a BACE455-selective inhibitor in the manufacture of a pharmaceutical composition for treating or preventing neurodegenerative diseases or an associated disorder in a subject.

As throughout this specification, most preferably the subject is a human subject.

The BACE455-selective inhibitor may be any agent, condition or treatment that reduces the expression or activity of a BACE455 polypeptide or a distinctive fragment thereof; or the expression, transcription or translation of a BACE455 nucleic acid or a distinctive fragment thereof in a subject. Most preferably, the BACE455-selective inhibitor is specific, i.e., preferentially alters the expression or activity of a BACE455 isoform and essentially does not directly alter expression of other BACE splicing isoforms. The inhibitors may, however, also affect wild-type BACE expression or activity to a greater or lesser extent.

BACE 455-selective inhibitors that exhibit 2-fold, or 5-fold, or 10-fold, or 30-fold, or 100-fold, and/or >1000 fold selectivity for inhibiting BACE455 activity vs. that of at least one other BACE isoform have an improved utility, compared to compounds that lack such selectivity or that significantly reduce the activity of wild-type BACE. Inhibitors that inhibit BACE455 activity and have a 2-fold or greater selectivity at inhibiting BACE455 as compared to wild type-BACE have a number of non-obvious benefits including (but not limited to) greater efficacy at inhibiting pathological disease progression, decreased side effects due to less inhibition of non-pathological Aβ production, and improved safety due to increased selectivity of compounds. Inhibitors can be used for the purpose of prophylactic or curative treatment of conditions including, for example, Alzheimer's disease and other conditions associated with elevated levels of Aβ 40 or 42 peptide, and the accumulation of the peptide in amyloid plaques. BACE455 inhibitors may be selected from peptides, proteins, nucleic acids, small drugs and the like. Typical examples include inhibitory nucleic acids and antibodies as disclosed above, as well as small drugs. Such drugs can be characterized or validated using screening approaches as disclosed below. They may be obtained from existing libraries of molecules or they can be designed using commercially available software programs and techniques familiar to those skilled in the art in organic chemistry and enzymology. Methods for making inhibitors may include (but may not limited to), combinatorial chemistry, screening of molecules libraries, rational drug design—these screening methods may employ BACE455 polypeptide or nucleic acids, or fragments of these, as elements of an assay for the selection of appropriate therapeutic candidates. Methods of inhibiting BACE455 may include, but not be limited to, the use of small molecule inhibitors, peptides, antisense oligonucleotides, iRNA, ribozymes, and blocking antibodies, i.e. agents that decrease BACE455 protein levels, activity or prevent cleavage of naturally occurring substrate in the brain.

In a particular embodiment, the BACE455 inhibitor is an antibody that binds BACE455. Antibodies can be produced by a variety of techniques that are known per se in the art. In particular, they may be produced by a method comprising immunizing a non-human animal with a BACE455 polypeptide or a distinctive fragment thereof, and collecting antibodies or antibody-producing cells from said animal. Antibodies may be monoclonals, polyclonals, as well as fragments or derivatives thereof having substantially the same antigen specificity (i.e., the ability to bind BACE455). Antibody fragments include Fab, Fab'2, CDR, etc. Antibody derivatives include single chain antibodies (ScFv), humanized antibodies, human antibodies, recombinant antibodies, bi-specific antibodies, etc. Techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in E. coli may also be used (Skerra et al., Science 242:1038-1041 (1988)). In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. A chimeric antibody is a molecule in which different portions are derived from different animal species, such as those having a variable region derived from a murine mAb and a human immunoglobulin constant region, e.g., humanized antibodies.

Human antibodies are desirable for therapeutic treatment of human patients. Human antibodies can be made by a variety of methods known in the art including phage display methods (Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT publications WO 90/02809; WO 91/10737) using antibody libraries derived from human immunoglobulin sequences. Methods of producing such antibodies are well know in the literature, as illustrated in the following, non limiting references: Harlow et al (Antibodies: A laboratory Manual, CSH Press, 1988; Ward et al (Nature 341 (1989) 544)). Most preferred antibodies selectively bind BACE455, e.g., bind an epitope that is distinctive of BACE455 as compared to other BACE isoforms.

In an other particular embodiment, the BACE455 inhibitor is an inhibitory nucleic acid that binds BACE455 gene or RNA, preferably BACE455 RNA, and inhibits or reduces the transcription or translation thereof. Such inhibitory nucleic acids can be produced as disclosed above. They preferably comprise a sequence that hybridizes to a distinctive fragment of a BACE455 RNA molecule, as disclosed above.

In an other embodiment, the BACE455 inhibitor is a selective inhibitor such as BACE inhibitor III (SEQ ID NO: 3).

BACE455 Inhibitors may be formulated in any suitable diluent, excipient, carrier or vehicle, that is compatible for pharmaceutical use. In this regard, the invention also contemplates a method of making a composition comprising a BACE455 inhibitor, the method comprising:
  i) selecting a compound that inhibits BACE455,
  ii) producing said compound, and
  iii) mixing said compound with a pharmaceutically acceptable salt thereof.

Compound that inhibits BACE of the present invention can be administered orally using any pharmaceutically acceptable dosage form known in the art for such administration. The vehicle may be any solution, suspension, powder, gel, etc., including isotonic solution, buffered and saline solutions, such as syrups or aqueous suspensions, etc. The compounds may be administered by any suitable route, including systemic delivery, intra-venous, intra-arterial, intra-cerebral or intrathecal injections. Repeated injections may be performed, if desired. The dosage can vary within wide limits and will have to be adjusted to the individual requirements in each particular case, depending upon several factors known to those of ordinary skill in the art. Agents determining the dosage of dosage the active compounds can be the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg. The daily oral dosage can vary from about 0.01 mg to 1000 mg, 0.1 mg to 100 mg, or 10 mg to 500 mg per day of a compound. The daily dose may be administered as single dose or in divided doses and, in addition, the upper limit can also be exceeded when this is found to be indicated.

The compounds of the present invention can be administered in such oral dosage forms as tablets, capsules (each of which can include sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to prevent or treat neurological disorders related to .beta.-amyloid production or accumulation, such as Alzheimer's disease and Down's Syndrome.

The compounds can be administered alone, but is generally administered with a pharmaceutical carrier, with respect to standard pharmaceutical practice (such as described in Remington's Pharmaceutical Sciences, Mack Publishing).

Compound that inhibits BACE455 can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents, either administered alone, or administered with a pharmaceutical carrier selected on the basis of the chosen route of administration and standard pharmaceutical practice.

The compound that inhibits BACE455 for the present invention can be administered in intranasal form via topical use of suitable intranasal vehicles, or via transdermal routes, using those forms of transdermal skin patches wall known to those of ordinary skill in that art.

Oral administration in the form of a tablet or capsule containing the active compound can be combined with an oral, non-toxic, pharmaceutically acceptable, inert carrier such as lactose, starch, sucrose, glucose, methyl callulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Sweetening agents such as those set forth above, and flavoring agents may be added to provide a palatable oral preparation. These compositions may be preserved by the addition of an anti-oxidant such as butylated hydroxyanisol or alpha-tocopherol. Suitable binders include starch, gelatin, natural sugars such as glucose or .beta.-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methyl cellulose, agar, bentonite, xanthan gum, and the like.

Compound that inhibits BACE455 can also be administered in the form of liposomal particulate delivery systems, such as small unilamellar vesicles, large unilamallar vesicles, and multilamellar vesicles. Liposomes can be formed from a variety of phospholipids, such as cholesterol, stearylamine, or phosphatidylcholines. Alternatively, compounds of the present invention may also be coupled with soluble polymers as targetable drug carriers, such as polymers made of polyvinylpyrrolidone, pyran copolymer, polyhydroxypropylmethacrylamide—phenol, polyhydroxyethylaspartamide—phenol, or polyethyleneoxide—polylysine substituted with palmitoyl residues. Polymers may also belong to the class of biodegradable polymers useful in achieving controlled release of a drug, for example, polylactic acid, polyglycolic acid, copolymers of polylactic and polyglycolic acid, poly-epsilon caprolactone, polycyanoacylates, etc. . . . or block copolymers of hydrogels.

Compounds for the present invention may be formulated into gelatin capsules with the addition of lactose, starch, cellulose derivatives, magnesium stearate, stearic acid, and the like as powdered carriers. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfate, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol. The therapeutic compositions and methods of this invention can be used to inhibit the progression of pathological diseases such as (but not limited to), Alzheimer's, dementia, glaucoma, Parkinson's, ALS, and stroke. Within the context of this invention, the term "treatment" designates preventive or curative treatments of neurological disorders, including at early or late stages of progression. Treatment includes delaying disease progression, reducing Aβ peptide production or accumulation, ameliorating the patients' condition, etc. Treatment can be used alone or in combination with other active agents.

Drug Screening

In another embodiment, the present invention also provides novel targets and methods for the screening of drug candidates or leads. The methods include binding assays and/or functional (activity) assays, and may be performed in vitro, in cell systems, in animals, etc.

A particular object of this invention resides in a method of selecting, characterizing, screening or optimizing a biologically active compound, said method comprising contacting in vitro a test compound with a distinctive BACE455 nucleic acid, polypeptide, or fragment of one of these, and determining the ability of said test compound to bind and/or influence the activity of said BACE455 nucleic acid or polypeptide. Binding alone provides some indication as to the ability of the compound to modulate the activity of said target, (although non-binding allosteric inhibitors may also be useful in, and are included within the scope of, the therapeutic methods of the present invention) and thus to affect a pathway leading to neurodegenerative disorders. In a presently preferred embodiment, the method comprises contacting in vitro a test compound with a distinctive BACE455 polypeptide or fragment thereof and determining the ability of said test compound to bind said polypeptide or fragment. The fragment preferably comprises an isoform-specific domain and/or a catalytic domain.

The determination of binding may be performed by various techniques, such as by labelling of the test compound, by competition with a labelled reference ligand, or other direct or indirect means of detecting a binding complex.

A further embodiment of the present invention resides in a method of selecting, characterizing, screening or optimizing a biologically active compound, said method comprising contacting in vitro a test compound with a BACE455 polypeptide and determining the ability of said test compound to modulate the activity of said polypeptide. In a specific embodiment, the test compound is contacted with a BACE455 polypeptide in the presence of BACE substrate (e.g., APP or an appropriate fragment thereof), and any changes in BACE455 activity, for example, proteolytic activity) is observed. In a preferred embodiment, the method comprises determining whether the test compound selectively affects BACE-mediated hydrolysis of the substrate. Typically, the test is carried out using a cell (e.g., a recombinant host cell) that expresses a BACE455 polypeptide.

A further embodiment of this invention resides in a method of selecting, characterizing, screening and/or optimizing a biologically active compound, said method comprising contacting a test compound with a BACE455 RNA and determining the ability of said test compound to modulate the translation of said BACE455 RNA.

Selectivity of the compound may be assessed by determining the effect thereof on other BACE splice isoforms that contain a full length exon 4.

The above screening assays may be performed in any suitable device, such as plates, tubes, dishes, flasks, etc. Typically, the assay is performed in multi-well microtiter dishes. Using the present invention, several test compounds can be assayed in parallel. Furthermore, the test compound may be of various origin, nature and composition. It may be any organic or inorganic substance, such as a lipid, peptide, polypeptide, nucleic acid, small molecule, in isolated or in mixture with other substances. The compounds may be all or part of a combinatorial library of compounds, for instance.

Further aspects and advantages of this invention will be disclosed in the following examples, which should be regarded as illustrative and not limiting the scope of this application. The entire contents of all publications, patents or patent applications cited throughout the present specification and examples is incorporated therein by reference.

EXAMPLES

Example 1

DATAS Technology Identifies Alternative Splicing Events in Human BACE

The DATAS technology for expression profiling studies (detailed in e.g., U.S. Pat. No. 6,251,590, hereby incorporated by reference herein) was used to compare alternatively spliced RNA present in the prefrontal cortex of well characterized AD patients and healthy controls. Control subjects were non-demented, were age-matched and the brain tissue was of similar age post-mortem to filter out age-related and mRNA stability-related changes in profiling studies.

The EXH-NADC5033 DATAS fragment aligns with NM_012104, which contains the coding sequence of the BACE501 protein (variant a isoform). Due to the differences in these two sequences, the existence of EXH-NADC5033 variant indicates a dysregulation of normal RNA splicing events in the brain of patients suffering from AD.

Through various alternative splicing events at the level of Exon 3 and 4 in the BACE sequence, different isoforms have been previously described (transcript variant-a to -d) (Bodendorf et al., J Biol. Chem. 276(15):12019-12023 (2001), Zohar et al., Brain Res Mol Brain Res. 115(1):63-68 (2003), Tanahashi and Tabira, Neurosci Lett. 307(1):9-12 (2001), hereby incorporated herein by reference).

The following primers were used to confirm the existence of alternative RNA splice events associated with this DATAS fragment:

PR_NM_012104-F01 (position on BACE501 coding sequence 3760-3780) (SEQ ID NO: 26) and PR_NM_012104-R01 (position on BACE501 coding sequence 4312-4330) (SEQ ID NO: 27) for the amplification of nucleic acid fragments encompassing the DATAS fragment and PR_NM_012104-F02 (position on BACE501 coding sequence 698-716) (SEQ ID NO: 28) and PR_NM_012104-R02 (position on BACE501 coding sequence 1158-1178) (SEQ ID NO: 29) for the amplification of nucleic acid fragments encompassing the RNA region subjected to previously identified alternative splicing events (transcript variant-a to -d) (Bodendorf et al., J Biol. Chem. 276(15):12019-12023 (2001), Zoharet al., Brain Res Mol Brain Res. 115(1):63-68 (2003), Tanahashi and Tabira, Neurosci Lett. 307(1):9-12 (2001)).

Total RNA from human brain isolated from prefrontal cortex of well characterized AD patients was isolated using Trizol (Invitrogen). One microgram of RNA was reverse transcribed in 35 µL using Superscript RT kit (Invitrogen) at 42 degrees C. for one hour, followed by an incubation with 1 µl RNAse One (Promega) for 15 min at 37 degrees C. PCR were conducted on $1/10^{th}$ of the reverse transcripts with 1.5 mM MgCl2, 0.2 mM dNTP, 1 µM of each primer. Conditions were: 3 min at 94 degrees C. and 30 cycles of 94 degrees C. for 30 seconds, 60 degrees C. for 30 seconds and 72 degrees C. for 45 seconds. After a final elongation of 5 min at 72 degrees C., PCR fragments corresponding to the full length cDNAs were analyzed on a 1.5% agarose gel, cloned into TOPO TA vector using the TOPO TA cloning kit (Invitrogen) and ligation products were transformed into TOP10 E. Coli cells (Invitrogen). Cells were grown in 96 well plates overnight at 37 degrees C. and colonies were picked and amplified overnight at 37 degrees C. in 2XTY bacterial culture medium in the presence of ampicillin.

Prior to sequencing, a PCR using SP6 and T7 primers (1 µM each, Invitrogen) were conducted at 55 degrees C. for 30 cycles on 1 µl aliquot of each culture. Five µl of the PCR reaction were run on a 1.5% agarose gel, and the remaining of the PCR products were purified on P100 Bio-Gel (Biorad) columns. Sequence reaction was conducted using ABI Prism Big Dye Terminator Cycles Sequencing Ready Reaction kit version 3.0 (Aplera) and reaction products were purified on G50 Sephadex columns (Amersham) and analyzed on a 3100 Genetic Analyser sequencer (Applied Biosystems).

Batch cloning and sequencing of all PCR products revealed the existence of two different transcripts corresponding to BACE501 transcript variant a and b plus a new isoform.

Analysis of the protein encoded in part by the DATAS fragment was deduced, assuming that the DATAS fragment was the locus of variation between BACE501 and BACE455. This protein shows high homology to the aspartic proteinase 2 BACE (or ASP2) described by Sinha et al., Nature 402, 537-540 (1999) and Vassar et al., Science 286, 735-741 (1999), both of which are incorporated by reference herein. Searches in various public ETSs databases such as Genbank, DDBJ (DNA Data Bank of Japan), and EMBL (European Molecular Biology Laboratory) using publicly available bioinformatic tool such as BLAT (Kent, Genome res. 12: 656-664 (2002)) or using the commercially available DoubleTwist Annotated Human Genome Database and the DoubleTwist Annotated Human and Mouse Gene Indices (produced by DoubleTwist, Inc.) failed to identify the new transcript isoform. The new transcript isoform was named BACE455 following the nomenclature from the literature (Bodendorf et al., J Biol. Chem. 276(15):12019-12023 (2001), Zohar et al., Brain Res Mol Brain Res. 115(1):63-68 (2003), Tanahashi and Tabira, Neurosci Lett. 307(1):9-12 (2001)). Based on alignment with BACE501 and other isoforms, it was determined that BACE455 transcript lacks exon4.

Example 2

Molecular Cloning of Human BACE455, a New Alternatively Spliced Form of BACE

The full length BACE501 cDNA and the cDNA of BACE455 were subsequently cloned from the same starting material from Alzheimer brain using the GC-RICH-PCR-system (Roche Molecular Biochemicals). (Capell et al., J. Biol. Chem. 275: 40, 30849-30854 (2000)). Reverse transcribed RNA (see Example 1) were amplified with the following primers: PR_NM_012104-F03 (position on BACE501 coding sequence 442-459) (SEQ ID NO. 6) and PR_NM_012104-R03 (position on BACE501 coding sequence 1971-1984) (SEQ ID NO. 7) used at the concentration of 1 µM in the presence of 1.5 mM MgCl2, using the manufacturer's specifications. PCR products corresponding to the full length cDNAs of BACE501 and BACE455 were cloned into TOPO TA vector as described in Example 1 and sequenced using SP6 and T7 primers and primers PR_NM_012104-F01 (SEQ ID NO: 26), PR_NM_012104-F02 (SEQ ID NO: 28) and PR_NM_012104-R02 (SEQ ID NO: 29).

To enrich the cDNA population in cDNA corresponding to BACE455 isoform, 20 µl of the first strand reverse transcripts reaction was subjected to second strand synthesis in Second Strand Buffer (Gibco) containing DNA polymerase I, dNTP mix 10 mM, RNase H (E. Coli, Gibco) and DNA ligase (E. Coli, Gibco) for 2 hrs at 16 degrees C. Then, double strand cDNA (dscDNA) were Phenol/Chlorophorm/Isoamyl alcool (24:25:1, v/v)—extracted and precipitated. dscDNA were then digested with restriction enzymes, Stu1 or Bcl1 (New England Biolabs). The digestion reaction was conducted for 2 hrs at 37 degrees C. in 20 µl using one fifth of the purified dscDNA reaction product. Bace 455 can not be cut by Stu1 or Bcl1, which cut in the deleted DNA fragment, while BACE501 is digested and can not be amplified by PCR. BACE455 was PCR amplified (60° C., 30 cycles) using primers PR_NM_012104-F03 (position on BACE501 coding sequence 442-459) (SEQ ID NO: 30) and PR_NM_012104-R03 (position on BACE501 coding sequence 1971-1984) (SEQ ID NO: 31) used at the concentration of 1 µM in the presence of 1.5 mM MgCl2SP6 and T7 primers and primers PR_NM_012104-F01 (SEQ ID NO: 26), PR_NM_012104-F02 (SEQ ID NO: 28) and PR_NM_012104-R02 (SEQ ID NO: 29). PCR product corresponding to the full length cDNA was analyzed on a 1.5% agarose gel, subcloned into TOPO TA vector as described in Example 1 and sequenced.

After full length cloning and sequencing, the full length nucleotide (SEQ ID NO: 1) and predicted amino acid (SEQ ID NO: 2) sequences of BACE455 were determined. Results and alignments are shown in FIG. 1.

BACE501 was also cloned from an EST found in the EST IMAGE database: BC036084, clone MGC:33762. The corresponding bacterial strain # MHS1010 containing the EST sequence was obtained from Open Biosystem (Huntsville, Ala.). PCR were conducted using the GC-RICH-PCR-system (Roche Molecular Biochemicals), using the manufacturer's specifications and primers PR_NM_012104-F03 (SEQ ID NO: 30) and PR_NM_012104-R03 (SEQ ID NO: 31) at 1 µM and 1.5 mM MgCl2. PCR products were analysed on a 1.5% agarose gel and cDNA corresponding to the full length sequence were cloned into TOPO TA vector as described in Example 1 and sequenced using SP6 and T7 primers and primers PR_NM_012104-F01 (SEQ ID NO: 26), PR_NM_012104-F02 (SEQ ID NO: 28) and PR_NM_012104-R02 (SEQ ID NO: 29).

The new BACE variant named BACE455 completely lacks the BACE501 exon 4, resulting from an in-frame 138 by deletion located between the two active aspartate residues within the solvent-exposed α-helix bridging the two extracellular lobes of the BACE501 protein (amino acid residues 190 to 235). Based on the BACE501 crystal structure published by Hong et al., Science. 290(5489):150-3 (2000), it appears that the active site of BACE455 is more open and accessible and is therefore likely to produce significantly increased levels of Aβ peptide.

The new shorter protein contains 455 amino acid residues and has a theoretical molecular weight of about 50 kDa. BACE455 contains the pro-region, an aspartic protease region, the trans-membrane region near the C-terminus and the N-linked glycosylation site essential for correct BACE processing (Asn153 and Asn 172) system (Fluhrer, R. et al.; J Biol. Chem. 278(8):5531-5538 (2003), Haniu, M. et al. J. Biol. Chem. 275:21099-106 (2000)), suggesting that the novel BACE455 variant is correctly processed and matured in the secretory pathway. The active enzyme is BACE455 and the pro-enzyme is pro-BACE455.

Recent data by Huse et al. (J Biol. Chem. 278(19):17141-9 (2003)) have demonstrated that BACE β-secretase activity is partially terminated by endoproteolytic cleavage of BACE1. This recently discovered process occurs on the α-helix between the two extracellular lobes (between Leu228 and Ala229) of BACE. Cleavage at this site by an unknown protease has been reported to result in the generation of distinct N- and C-terminal fragments each of ~37 kD in size. The two fragments are apparently maintained in a pseudo-active conformation by disulfide bonds, leading to a significantly attenuated, but not abolished, enzymatic activity. Importantly, BACE455 is not a substrate for this endoproteolytic processing, since this region is encoded by the deleted exon4.

Example 3

BACE455 Shows Comparable Immunoreactivity with that of BACE501 in Transfected Mammalian Cells BACE has a half-life in the cell of greater than 9 h (Haniu et al., J. Biol. Chem. 275: 21099-21106 (2000)) and cycles several times to the membrane during this period of time. Therefore, using antibodies specific of its N-terminal portion, BACE can be immunolocalized at the cell surface of intact cells (i.e. non permeabilized) and inside the cell (Golgi and endosomal compartments) in permeabilized cells. In contrast, BACE variants such as BACE457 which are inactive and whose transport along the secretory pathway is deficient and blocked at the level of the endoplasmic reticulum, can not be detected at the cell surface (Bodendorf et al., J Biol. Chem. 276: 2019-23 (2001)). Therefore, immunohistochemistry studies can determine whether a given BACE variant such as BACE455 is present at the same intracellular sites as APP, or both intracellular and extracellular as BACE501, which is a prerequisite for its amyloidogenic activity.

Material and Methods

To create pCDNA3-based expression vectors, full length cDNA of BACE501 and BACE455 in TOPO TA vector were subcloned into pcDNA3 (Invitrogen) at the EcoR1 site to create pcDNA3-BACE501 and pcDNA3-BACE455, respectively. The cDNA (200 ng plasmid/sequencing reaction) were sequenced for verification and orientation of the insert using SP6 and T7 primers from Invitrogen using the protocol described in Example 1.

NIH3T3 cells (ATCC # CRL 1658) were used to study BACE immunoreactivity because of the large size of their cytoplasm and their murine origin. Cells are routinely grown at 37° C. and 5% $CO_2$ in Dulbecco's modified Eagle's medium with 4.5 g/l glucose and supplemented with 10% newborn bovine serum, 1% penicillin/streptomycin in T150 culture flasks. Cells are plated at 40.000 cells/well of a 6-well plate the day before transfection. Transient transfection experiments are performed with pcDNA3-BACE501, pcDNA3-BACE455 or pcDNA3-GFP (1 µg vector/well) and the Lipofectamine Plus reagent (Life Technologies) using the manufacturer's recommendations. Two days after transfection, cells are processed for immunolocalization or functional assays.

Transfected cells are cultured on poly-D-lysine-coated glass coverslips. For immunostaining, cells are fixed in 3% paraformaldehyde at 20° C. Cells were either permeabilized with Triton X100 (0.1% in PBS) or processed intact (no permeabilization). After blocking with 3% bovine serum albumin in phosphate buffered saline, permeabilized or intact cells are incubated with the rabbit anti-human BACE antibodies raised against the aminoacid sequences 46-65 or 487-501 (Calbiochem) at 1:800 dilution. Cy3- or FITC-conjugated secondary antibodies (Sigma) are used at 1:800 dilution. Stained cells are embedded in Fluor Save (Calbiochem).

Results

It is apparent from our results that BACE455 presents a comparable immunoreactivity to that of BACE501 both at the cell surface and in subcellular compartments (FIG. 2). This indicates that exon 4 deletion in BACE455 does not affect its transport because BACE is efficiently exported to the cellular membrane. As BACE intracellular transport is intimately linked to processing and maturation, it is likely that BACE455 processing and maturation is not altered either and, consequently, that BACE455 amyloidogenic activity is not impaired when compared to that of BACE501.

Example 4

Demonstration of BACE455 Activity on Peptide Substrates

Two experiments were performed which demonstrate BACE455 activity on APP-based peptide substrates encompassing the beta site of cleavage. The amino acid sequence of the substrates corresponds to APP and mimics the mutation in APP found in a Swedish kindred with inherited AD in which KM amino acid residues are changed to NL. The Swedish mutation is known to increase cleavage of APP by the beta-secretase. In the first experiment, increased expression of BACE455 in transfected human embryonic kidney HEK293 is shown to increase cleavage of the synthetic fluorogenic substrate. A second set of experiments demonstrate that BACE455 exhibits similar activity efficiency in fluorogenic assay than BACE501. To do so, the well characterized human embryonic kidney HEK293 cell line in a practical tool to study the function of overexpressed proteins.

Material and Methods

Mammalian Cell Transfection and Clone Selection:

Human embryonic kidney HEK293 cells (ATCC # CRC-1573) were transfected with expression constructs using the Lipofectamine Plus reagent from Invitrogen. Cells were seeded in 10 cm culture plates to a density of 70-80% confluence. Each plate was transfected with 2 DNA, 8 µl Plus reagent, and 4 µl Lipofectamine in OptiMEM. After 5 h incubation, the transfection media was replaced with DMEM, 10% FBS, NaPyruvate, with antibiotics and the cells were incubated under normal conditions (37 [deg.] C., 5% CO2) for 72 hours. Three days post-transfection, cells were passaged into medium containing G418 at a concentration of 400 µg/ml. After fifteen days growth in selective medium, individual clones were selected plated into each well of one 96 well plate containing growth medium plus G418. Clones were expanded from the 96 well plate to a 24 well plate and then a 6 well plate. BACE455 or BACE501 expression in selected clones was assayed by Western Blotting and immunohistochemical analysis using C-terminal-specific antibody as in Example 3. The final BACE455 or BACE501 cell lines selected exhibited the highest expression level of BACE455 or BACE501, respectively.

Preparation of Cell Extracts, Fluorogenic Assay Protocol

Cells were harvested and centrifuged at 1,500 rpm for 5 minutes to remove the medium. The cell pellets were washed once with PBS. To further compare BACE455 activity with that of BACE501, an in vitro assay was developed based on quenched fluorogenic substrate (Substrate V, Calbiochem) containing the Swedish mutation KM->NL in APP. Sequence of the peptide was: MCA-SEVNLDAEFK(DNP)-CONH2 (SEQ ID NO: 32), containing the Swedish APP mutation (in boldface), 7-amino-4-methyl coumarin (MCA) as the fluorophore and dinotrophenol (DNP) as the quencher. When cell lysates of BACE455 and BACE501 expressing cells are incubated with the fluorogenic Substrate V, upon cleavage by the protease, the fluorophore is separated from the quenching group, restoring the full fluorescence yield of the donor. (Ermolief et al., Biochemistry 39: 12450-12456 (2000); Ellerby et al. J. Neurosci. 17: 6165-6178 (1997); Capel et al., J Biol. Chem. 277: 5637-43 (2002)).

Mock transfected HEK293 and HEK293-BACE455 and -BACE501cells were harvested by scraping in ice-cold 20 mM Tris/150 mM NaCl, pH 7.5 plus Complete Protease Inhibitor Cocktail (Roche Diagnostics). Cell were lysed by repeated freeze-thawing and a postnuclear fraction was generated after centrifugation at 500 g for 10 min. Pellets were resuspended in membrane extraction buffer (20 mM MES/ 1% Triton X100) containing protease inhibitor cocktail and incubated on ice for 30 minutes. The assay was carried out in black 96 well plates (ATGC) in a volume of 200 µl of the membrane preparation diluted in reaction buffer (25 mM MES/25 mM Sodium Acetate/25 mM Tris, pH 4.4) containing 15 µM peptide Substrate V. These components were equilibrated to 37 [deg.] C. for various times and the reaction initiated by addition of substrate. Excitation was performed at 320 nm and the reaction kinetics were monitored by measuring the fluorescence emission at 420 nm. To test the effect of pH, lysed cells were resuspended in 25 mM MES/25 mM Sodium Acetate/25 mM Tris adjusted at pH values ranging from 4.4 to 8 and then incubations were performed as above. Controls included purified recombinant human BACE501 protein (R&D Systems), or substrate alone and background fluorescence is subtracted to recorded BACE isoforms activities.

Results

BACE455 extracted from the membrane fraction generated a time dependent-increase in the fluorescent signal in the proteolysis assay, indicating that BACE455 possesses beta-secretase activity. Maximal proteolysis was seen after 2 hours, after which a plateau was reached, probably due to substrate depletion following complete cleavage.

analog inhibitor of BACE. It was previously shown to completely block the proteolytic activity in solubilized membrane fractions from BACE transfected cells (Capel et al., J. Biol. Chem. 277: 5637-43 (2002). Pepstatin A, Chymostatin, E64c, Leupeptin (Sigma) are inhibitors of cathepsin D (and other aspartyl proteases), or serine proteases and cysteinyl proteases, respectively.

Protease inhibitors were added to 100 µl reaction buffer (25 mM MES/25 mM Sodium Acetate/25 mM Tris, pH 4.4) at a final concentration of 100 µM. When indicated, the assay buffer had a pH ranging from 4.4 to 8. Membrane preparations were obtained as in Example 4 and incubated with the inhibitors for 10 min at room temperature. Reaction was then started by adding 100 µl of reaction buffer containing the substrate (15 µM final concentration) and monitored as described in Example 4. For the dose-response experiment of FIG. 3, Inhibitor III was assayed at various concentrations ranging from 100 µM to 100 nM Results There was a small inhibitable activity irrespective of BACE455 or BACE501 overexpression by non BACE-specific inhibitors. This can be attributed to other non-BACE membrane-bound proteases co-purified during this assay. However, in BACE455 or BACE501 extracts, substrate cleavage activity was overall very weakly sensitive to both the pepstatin and the other protease inhibitors, which are inhibitors of cathepsin D (and other aspartyl proteases), or serine and cysteinyl proteases, respectively. This suggests that non-BACE proteolytic activities contribution to substrate cleavage is minor. In contrast, BACE inhibitor III at 100 µM completely abolished BACE455 activity, as well as BACE501 activity, demonstrating the specificity for BACE-mediated cleavage of the fluorogenic substrate.

TABLE 2

BACE activity over time

| | Time (min) | | | |
|---|---|---|---|---|
| | 15 | 60 | 120 | 240 |
| BACE455 | 125.18 +− 13.1 | 195.48 +− 17.0* | 227.65 +− 15.0* | 238.86 +− 8.4* |
| BACE501 | 119.97 +− 16.4 | 192.36 +− 11.26* | 225.64 +− 23.23* | 249.41 +− 23.88* |
| Mock | 102.46 +− 7.58 | 134.96 +− 10.8 | 151.97 +− 11.3 | 158.28 +− 15.9 |

*p < 0.05, Wilkoxon test.
Shown results are mean fluorescence signals +− SEM of at least 3 independent experiments performed with BACE455, BACE501 or mock-transfected cells Example 5

Specificity of BACE455 Activity

BACE455 specificity on APP-based peptide substrates was assessed by performing the beta-secretase assay in the presence of a well characterized commercial BACE501 inhibitor, BACE inhibitor III. More important, using a dose response experiment, we show that BACE455 displays an inhibitory profile significantly different from that of BACE501.

Material and Methods

BACE inhibitor III (H-Glu-Val-Asn-Statine-Val-Ala-Glu-Phe-NH2) (SEQ ID NO: 33) from Calbiochem, is a substrate

TABLE 3

Percentage of BACE455 inhibition by various inhibitors

| | Inhibitor III | Pepstatin A | Chymostatin | E-64c | Leupeptin |
|---|---|---|---|---|---|
| BACE455 | 104.16 | 14.39 | 25.90 | 12.23 | 17.27 |
| BACE501 | 117.54 | 13.14 | 20.44 | 13.14 | 8.03 |

Shown results are mean percentage of cleavage inhibition +− SEM in BACE455, BACE501 or mock-transfected cell extratct plus the indicated inhibitor (100 µM each).

Figure 3:
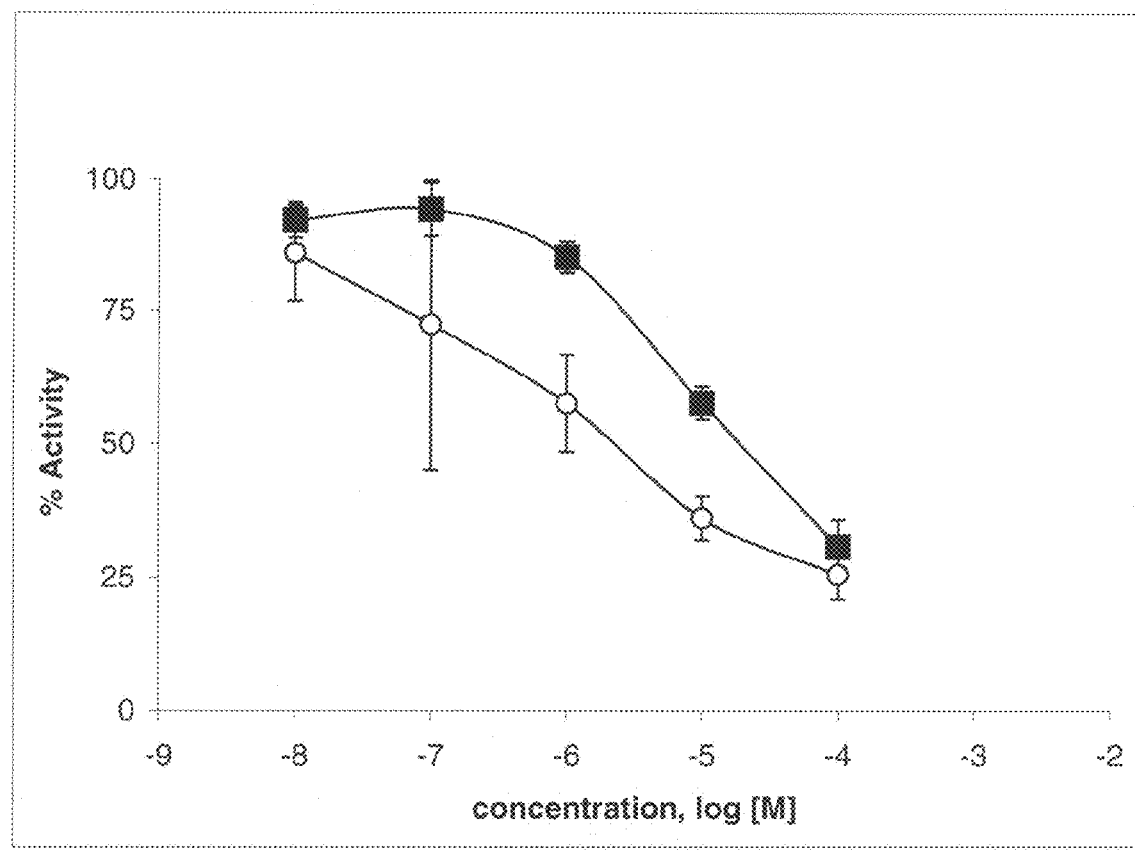
FIG. 3: BACE455 and BACE501 display different inhibitory profile using the commercially available BACE inhibitor III in the fluorogenic assay. Shown results are percentage of activity+−SEM in 3 independent experiments.

To further study BACE455 inhibitory profile and compare it to that of BACE501, a dose-response experiment was performed (see FIG. 3). At a concentration of 10 µM for Inhibitor III, BACE455 activity was 36.04+−4.13% (+−SEM) while BACE501 activity was 57.6+−3.12% (+−SEM) when compared to mock transfected control. At a concentration of 1 µM for Inhibitor III, BACE455 activity was 57.52+−9.08%

(+−SEM) while BACE501 activity was 85.15+−2.93% (+−SEM) when compared to mock transfected control. It is thus apparent that for a given concentration of inhibitor, BACE455 is less inhibited than BACE501, which suggests that BACE455 is significantly different from BACE501 in terms of inhibitory profile and that the deletion of exon4 in BACE455 generates a significant pharmacological difference when compared to BACE501.

Example 6

Acidic pH Requirement for BACE455 Activity

BACE is an acidic aspartyl protease mainly localized in the Golgi apparatus and in endosomal compartments and cleaves APP in these acidic compartments. BACE is virtually inactive at pH values of 6.0 and above ((Vassar R. et al. Science 286, 735-741 (1999); Lin X. et al. Proc. Natl. Acad. Sci. USA 97, 1456-1460 (2000)). Here, we present another argument for stating that the novel BACE455 variant presents true beta-secretase activity: the strong pH requirement which is observed by BACE-specific cleavage.

Material and Methods

Membrane preparations were obtained as in Example 4 and incubated in assay buffer (25 mM MES/25 mM Sodium Acetate/25 mM Tris) adjusted to final pH ranging from 4.4 to 8, in the presence or absence of BACE inhibitor III (100 μM final concentration). Reaction was started by adding 100 μl of reaction buffer (pH ranging from 4.4 to 8) containing the substrate (15 μM final concentration) and monitored as described in Example 4. We determined in these conditions the percentage of inhibition of BACE by Inhibitor III.

Results

Inhibitory activity of the BACE specific inhibitor was sharply maximal at pH 4.4. At pH 6 and 8, very high substrate cleavage activities were observed, unlike at pH 4.4, but were insensitive to the BACE commercial inhibitor. This is probably due to the recruitment of other proteases acting at pH6.0 or above, given that BACE is notoriously inactive at pH6 or above. These data indicate that this assay allows selective dosage of BACE455 and BACE501 secretase activity only at pH known in the literature to be relevant for BACE biological activity. In addition, the results demonstrate that BACE455 exhibits similar acidic pH dependency for activity than BACE501.

TABLE 4

Inhibitor-sensitive hydrolysis of Substrate V by BACE455 and BACE501-expressing cells is pH-dependent.

| | % Inhibition of BACE activity by Inhibitor III | | |
|---|---|---|---|
| | pH4.4 | pH 6.0 | pH 8.0 |
| BACE455 | 104.16 | 15.97 | 22.10 |
| BACE501 | 117.54 | 13.23 | 17.63 |

Shown results are mean percentage of cleavage inhibition in BACE455 or BACE501 cell extract performed with reaction buffeer adjusted to various pH.

Thus, BACE455 and BACE501, when similarly expressed in HEK293 cells and purified using identical conditions, also cleaves the Swedish beta-secretase peptide in proteolysis assays using identical assay conditions.

Example 7

Effects of BACE455 and BACE501 on Endogenously Expressed APP Isoforms Processing Proteolytic processing of APP is divided into an amyloidogenic and an antiamyloidogenic pathway. In the amyloidogenic pathway, cleavage of APP by BACE occurs at the N-terminus of the Aβ domain and yields the secreted sAPPβ as well as a C-terminal fragment of APP of 99 amino acids (C99) of 11,145 daltons molecular weight. C99 is further cleaved within its transmembrane domain by γ-secretase, leading to the secretion of the Aβ peptide and the generation of the APP intracellular domain AICD. In the antiamyloidogenic pathway, cleavage of APP by α-secretase within the Aβ peptide domain yields the neurotrophic and neuroprotective sAPPα.

Human cell lines that process Aβ peptide from APP provide a tool to screen in cellular assays for activators and inhibitors of beta-secretase. Although expression of APP, as well as endogenous APP processing and release of Abeta peptide are low, SH-SY5Y human neuroblastoma cell lines (ATCC, CRL-2266) are a useful system to detect APP processing and the generation of C99 and Aβ peptide.

Material and Methods

Mammalian Cell Transfection and Clone Selection:

SH-SY5Y cells for transfection were grown to 80% confluence in Dulbecco's modified Eagle's medium (DMEM) with 10% fetal bovine serum. Transfections were performed using LipofectAmine Plus (Gibco-BRL) with 4 pcDNA3 DNA per 10*10<6>cells. Three days posttransfection, cells were passaged into medium containing G418 at a concentration of 400 μg/ml. After twenty days growth in selective medium, individual clones were selected and plated into each well of one 96 well plate containing growth medium plus G418. Clones were expanded from the 96 well plate to a 24 well plate and then to a 6 well plate. Clones which had lost initial neuronal-like morphology were not amplified. BACE455 or BACE501 expression in selected clones was assayed by Western Blotting and immunohistochemical analysis using Cterminal-specific antibody. The final cell lines exhibited the highest expression level of BACE455 or BACE501 and have been maintained in G418 at 400 ug/ml with passage every four days into fresh medium.

Preparation of Cell Extracts, Western Blot Protocol

Cells were harvested 3 days after plating. Cells were washed twice with PBS and lysed in 1 ml CellLytic solution (Sigma) plus protease inhibitors cocktail (Roche Diagnostics) for 15 min. Lysates was transferred to 1.5 ml Eppendorf tube and centrifuged at 1,500 rpm for 5 minutes. The supernatants was stored at −80 [deg.] C. as the cell extracts. Equal amounts (20 μg) of extracts from cells transfected with the BACE455 or control vector (Mock) were electrophoresed through 12% Bis-Tris NOVEX gels (Invitrogen). Following electrotransfer of the separated polypeptides to PVDF membranes, APP and C99 proteolytic fragment were detected with C-terminal-specific rabbit anti-APP antibody (Serotec, UK) at 1/500 in PBS-Tween 20 0.1%, and the antibody-antigen complexes were visualized using alkaline phosphatase conjugated goat anti-rabbit antibodies (1/5000). The sequence recognised by the primary antibody corresponds to amino acids 85-99 of the C99 fragment. In cells, the primary antibody also detects a non specific band migrating around 45 kDa.

Results

Figure 4:
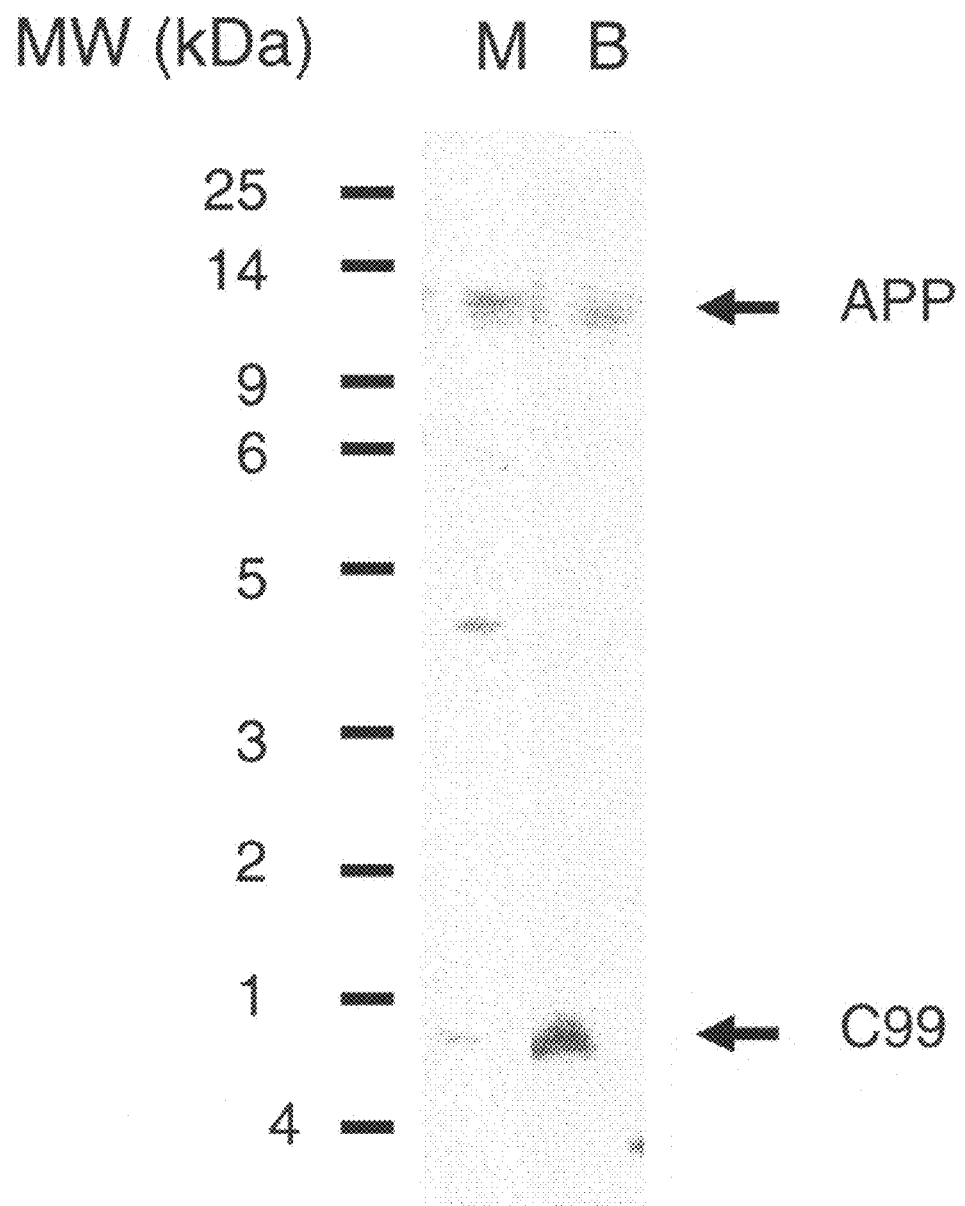
FIG. 4: Effects of BACE455 on the production of C99 fragment from endogenously expressed APP isoforms in SH-SY5Y cells transfected with the empty vector (Mock, M) or with a construct expressing BACE455 (B). MW: molecular weight

The effects of BACE455 on the production of C99 fragment from endogenously expressed APP isoforms were assessed in SH-SY5Y cells transfected with a construct expressing BACE455 or with the empty vector (Mock) after selection of transformants with the antibiotic G418 (FIG. 4). C99 production was strongly increased in cells transformed with the BACE455 construct in comparison to those transformed with the empty vector DNA. This corresponds to increased proteolysis of endogenous APP at residues Asp-1, in a manner similar to what is described for BACE501. Also, as reported in the literature for BACE501, the overexpression of BACE455 has no influence on APP levels.

Example 8

Inhibitory effect of Brefeldin A and Gleevec on BACE455-Dependent Processing of Endogenous APP Isoforms One way to interfere with BACE activity, but also APP processing, is the use of the fungal metabolite brefeldin A (BFA), which promotes fusion of the cis-, medial, and trans-Golgi (but not the TGN) with the ER (Lippincott-Schwartz et al. Cell 67: 601-616 (1991), or monensin, which disrupts traffic within the Golgi (Dinter et al. Histochem. Cell Biol. 109: 571-590 (1998)). Both drugs affect not only APP processing, but also BACE propeptide removal within the Golgi by inhibiting intracellular trafficking through the ER and the Golgi apparatus. As a result, in the presence of BFA, BACE overexpression leads to a reduced generation of C99 (Fischer et al. J. Neurochem. 80: 1079 (2002).

Gleevec (imatinib mesylate) is a selective tyrosine kinase inhibitor which can inhibit Aβ release because it blocks γ-secretase-mediated cleavage of APP (Netzer et al. Proc Natl Acad Sci USA 100: 12444-12449 (2003)). Gleevec is a Bcr-Abl inhibitor which controls cytoskeleton, axonal development, and dendrogenesis (Jones et al. J. Neurosci 24: 8510-8521 (2004)). Thus, Gleevec was tested as a pharmacological agent eventually controlling C99 generation by BACE, by impacting cell cytoskeleton and intracellular trafficking, thus preventing APP and BACE processing.

Materials and Methods

BACE455 SH-SY5Y cells were treated as in Example 7. Cells were harvested 3 days after plating and processed for Western Blotting experiments as described above. For BFA and Gleevec treatments, cells were treated at 10 μg/ml during the last 8 hours and at 10 μM for the last 24 hours, respectively.

Results

Figure 5:
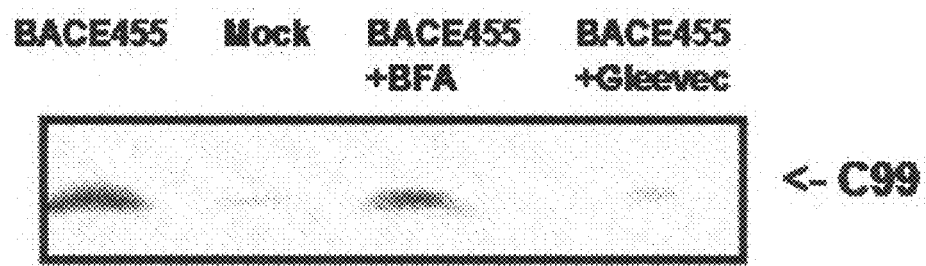
FIG. 5: C99 peptide generation from endogenously expressed APP isoforms in SH-SY5Y cells transfected with a construct expressing BACE455 is inhibited by Brefeldin A (BFA) and Gleevec.

To test if BFA interferes with C99 production in BACE455 cells in a manner similar to what has been reported with BACE501, BACE455 cells are treated with BFA or Gleevec and cell lysates are subjected to Western Blotting experiment using C-terminal-specific rabbit anti-APP antibody (FIG. 5). As expected, in the presence of BFA which affects not only APP processing, but also BACE processing, BACE overexpression leads to a reduced generation of C99. This shows that BACE455 displays similar processing through ER-Gilgi apparatus than that of BACE501.

Gleevec treatment of BACE455 cells also strongly reduced generation of C99 peptide, Although the mechanism of action is not clear, it can involve an effect on the localization of BACE or of APP in a way that prevents interaction of APP with BACE455, probably through modifications of intracellular transport and processing.

Example 9

Effects of BACE455 and BACE501 on the Production of Aβ Peptides from Endogenously Expressed APP Isoforms Human cell lines that process Aβ peptide from APP provide a tool to screen in cellular assays for activators and inhibitors of beta-secretase. Multiple subcellular sites are responsible for the production of different Aβ peptides. The trans-Golgi network produces predominantly Aβ 1-40 (Xu et al., Proc. Natl. Acad. Sci. U.S.A. 94: 3748-3752 (12997), Hartmann et al., Nat. Med. 3: 1016-1020 (1997)), although the endoplasmic reticulum/intermediate compartment produces Aβ1-42 (Lee et al., J. Biol. Chem., Vol. 278: 4458-4466 (2003), Greenfield et al. Proc. Natl. Acad. Sci. U.S.A. 96, 742-747 (1999)). Production and release of Aβ peptide into the culture supernatant can be monitored by an enzyme-linked immunosorbent assay (ELISA). Although expression of APP, as well as endogenous APP processing and release of Abeta peptide are low, SH-SY5Y human neuroblastoma cell lines (ATCC, CRL-2266) are a useful system to detect Abeta processing. To do so, an isoform-specific ELISA designated for the in vitro quantitation of Aβ in cell extract, serum, culture medium can be used. An example of ELISA kit is the isoform-specific Aβ1-40 ELISA from BioSource International. Typically, SH-SY5Y cells cultured in normal conditions secrete around 40 pg/ml of Abeta 1-40, which is well in the detection limits and linear range of the assay (Takahashi et al., J. Biol. Chem. 278: 18664-70 (2003)). In contrast, the generation of Abeta 1-42 is weaker than Abeta 1-40 and thus cannot be detected without overexpressing APP.

Aβ ELISA Analysis (Double Antibody Sandwich ELISA for Abeta 1-40):

Cell culture supernatants harvested 72 hours after plating were analyzed in a standard double antibody isoform-specific Aβ1-40 ELISA (BioSource International) as follows. The capture rabbit antibody is specific to an epitope present on Abeta and has been coated to a 96 well immunoplate. The detecting antibody is specific for Abeta 1-40 and the conjugated secondary antibody is an anti-rabbit IgG conjugated to horseradish peroxydase. Synthetic human Aβ1-40 standard peptides are serially diluted in the supplied sample diluent for the generation of standard curves. Concentrations of the peptides after dilution were: 1000, 500, 250, 125, 62.5, 31.3, 15.6 and 0.0 pg/ml in a volume of 100 μl/well.

For quantitation in conditioned medium, 5 ml of DMEM with 1 μM of the metalloendoproteinases inhibitor phosphoramidon is conditioned for 17 h by one 10 cm plate of $3.5*10^6$ SH-SY5Y cells (plating density) and centrifuged at low speed for 5 min to remove cellular debris (Haugabook et al., J. Neurosci. Methods. 108:171-179 (2001)). Human Abeta 1-40 standards were added after washing the plate, as well as 100 μl/well of sample, e.g., conditioned medium of transfected cells. The plate was incubated at 4 [deg.] C. overnight. The next day, after washing the plate four times, 100 μl/well rabbit detection antibody was added and incubated for 2 hours on an orbital plate shaker at 20 degree C. Following four washes, 100 μl/well anti-rabbit IgG-horseradish peroxidase antibody (diluted 1:100) was applied and incubated for 2 hour at room temperature with shaking. After the last five washes 100 μl/well of tetramethylbenzidine was added as chromogen substrate and the color development was allowed for 20 min at room temperature in the dark. 100 μl/well stop solution was added and absorbance of each well was read at 450 nm within two hours, with a solution of 100 μl each of chromogen and stop solution as the blank. All standards and samples were run in triplicates. The samples with absorbance values falling within the standard curve were extrapolated (by comparison to the values obtained for the A-β40 and A-β42 standard peptides analyzed on the same plate) from the standard curves and expressed in pg/ml culture medium.

Results

Effects of BACE455 or BACE501 on the production of Abeta peptides from endogenously expressed APP were assessed in SH-SY5Y cells transfected with a construct expressing BACE455 or BACE501 or with the empty vector (Mock) after selection of transformants with the antibiotic G418. Aβ1-40 production was increased two times in cells transformed with the BACE455 or BACE501 construct in comparison to those transfected with the empty vector DNA. Aβ1-40 levels in conditioned medium collected from cells transfected with a the empty vector were 43.21+1.46 pg/ml, a value well within the linear range of the assay. Aβ1-40 release, expressed as the percentage of control (cells transfected with the empty vector DNA), from cells transfected with BACE455 or BACE501 was 199.95+18%, and 193.15+2.73 respectively (p<0.001 for both). This indicates that BACE455 acts to facilitate the processing and release of Aβ from endogenously expressed APP, as does BACE501.

In the presence of BFA which affects not only APP processing, but also BACE processing, and C99 fragment generation of which Aβ1-40 is derived, Aβ1-40 levels in conditioned medium were similar to that of mock transfected cells. Gleevec treatment of BACE455 cells also strongly reduced Aβ1-40 release. Gleevec has been shown to block γ-secretase-mediated cleavage of APP (Netzer et al. Proc Natl Acad Sci USA 100: 12444-12449 (2003)), which is required to generate Aβ1-40. Thus, our results show that Gleevec effect not only involves a reduction of γ-secretase-mediated cleavage of APP, but results from an effect on intracellular transport and processing i.e. on the localization of BACE or of APP in a way that prevents interaction of APP with BACE455.

Collectively, these data establishes that BACE455 act directly to cleave APP at the beta-secretase site, and that the rate of cleavage does not significantly differ between this isoform and BACE501 within cells. However, BACE455 activity depends on intracellular transport and processing and can be inhibited by Brefeldin A and Gleevec. BACE455 thus is an active APP-cleaving protease expressed in the brain of patients with Alzheimer's disease. Thus, the Applicants believe that BACE455 causes the accumulation of amyloidogenic Aβ peptides responsible for the development of Alzheimer's disease.

TABLE 5

Results of transfecting BACE455 or BACE501 plasmid DNA on release of Aβ

|  | Aβ release (% of control) |
|---|---|
| Control | 100 |
| BACE501 | 193.15 +− 2.73* |
| BACE455 | 195.46 +− 17.42* |
| BACE455 + 10 μg/ml BFA | 95.15 +− 5.06 |
| BACE455 + 10 μM Gleevec | 111.56 +− 6.20 |

*p < 0.05, Wilkoxon test.

Values tabulated are percentage of Aβ relase +− SEM, with control set as 100%

TABLE 1

List of primer sequences

| Sequence identifier | Sequence description |
|---|---|
| SEQ ID NO. 26 | PCR primer PR_NM_012104-F01 (position on Refseq 3760–3780, exon1) |
| SEQ ID NO. 27 | PCR primer PR_NM_012104-R01 (position on Refseq 4312–4330, exon9) |
| SEQ ID NO. 28 | PCR primer PR_NM_012104-F02 (position on Refseq 698–716, exon5) |
| SEQ ID NO. 29 | PCR primer PR_NM_012104-R02 (position on Refseq 1158–1178, exon9) |
| SEQ ID NO. 30 | PCR primer PR_NM_012104-F03 (position on Refseq 442–459, exon1) |
| SEQ ID NO. 31 | PCR primer PR_NM_012104-R03 (position on Refseq 1971–1984, exon9) |
| SEQ ID NO. 32 | fluorogenic APP-based peptide MCA - SEVNLDAEFK(DNP) - CONH2 |
| SEQ ID NO. 33 | BACE inhibitor III H-Glu-Val-Asn-Statine-Val-Ala-Glu-Phe-NH2 |

Position on Refseq (NCBI Reference Sequences) refers to the position of the primer on the BACE501 nucleotidic sequence (NM_012104). RefSeq is a reference for gene identification and characterization, mutation analysis, expression studies, polymorphism discovery, and comparative analyses. The Reference Sequence (RefSeq) collection provides a comprehensive, integrated, non-redundant set of sequences, including genomic DNA, transcript (RNA), and protein products, for major research organisms.

The invention claimed is:

1. An isolated monoclonal antibody, fragment or derivative thereof that specifically binds to a polypeptide consisting of the sequence of SEQ ID NO: 5, wherein said fragment is a Fab fragment, a Fab'2 fragment, or a CDR fragment, and wherein said derivative is a single chain antibody, human antibody, humanized antibody, or a recombinant antibody.

* * * * *

SEQUENCE LISTING

<160> NUMBER OF SEQ ID NOS: 36

<210> SEQ ID NO 1
<211> LENGTH: 1368
<212> TYPE: DNA
<213> ORGANISM: Homo sapiens

<400> SEQUENCE: 1
atggcccaag ccctgccctg gctcctgctg tggatgggcg cgggagtgct gcctgcccac        60
ggcacccagc acggcatccg gctgcccctg cgcagcggcc tggggggcgc ccccctgggg       120

```
ctgcggctgc cccgggagac cgacgaagag cccgaggagc ccggccggag gggcagcttt      180
gtggagatgg tggacaacct gaggggcaag tcggggcagg gctactacgt ggagatgacc      240
gtgggcagcc ccccgcagac gctcaacatc ctggtggata caggcagcag taactttgca      300
gtgggtgctg ccccccaccc cttcctgcat cgctactacc agaggcagct gtccagcaca      360
taccgggacc tccggaaggg tgtgtatgtg ccctacaccc agggcaagtg ggaaggggag      420
ctgggcaccg acctggtaag catcccccat ggccccaacg tcactgtgcg tgccaacatt      480
gctgccatca ctgaatcaga caagttcttc atcaacggct ccaactggga aggcatcctg      540
gggctggcct atgctgagat tgccaggatc attggaggta tcgaccactc gctgtacaca      600
ggcagtctct ggtatacacc catccggcgg gagtggtatt atgaggtcat cattgtgcgg      660
gtggagatca atggacagga tctgaaaatg gactgcaagg agtacaacta tgacaagagc      720
attgtggaca gtgcaccac caaccttcgt ttgcccaaga agtgtttga agctgcagtc      780 aaatccatca aggcagcctc ctccacggag aagttccctg atggtttctg ctaggagag      840 cagctggtgt gctggcaagc aggcaccacc ccttggaaca ttttcccagt catctcactc      900
tacctaatgg gtgaggttac caaccagtcc ttccgcatca ccatccttcc gcagcaatac      960
ctgcggccag tgaagatgt ggccacgtcc aagacgact gttacaagtt tgccatctca     1020
cagtcatcca cgggcactgt tatgggagct gttatcatgg agggcttcta cgttgtcttt     1080
gatcgggccc gaaaacgaat tggctttgct gtcagcgctt gccatgtgca cgatgagttc     1140
aggacggcag cggtggaagg ccctttttgtc accttggaca tggaagactg tggctacaac     1200
attccacaga cagatgagtc aaccctcatg accatagcct atgtcatggc tgccatctgc     1260
gccctcttca tgctgccact ctgcctcatg gtgtgtcagt ggcgctgcct ccgctgcctg     1320
cgccagcagc atgatgactt tgctgatgac atctccctgc tgaagtga                 1368
```

<210> SEQ ID NO 2
<211> LENGTH: 455
<212> TYPE: PRT
<213> ORGANISM: Homo sapiens

<400> SEQUENCE: 2

```
Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
                20                  25                  30

Gly Leu Gly Gly Ala Pro Leu Gly Leu Arg Leu Pro Arg Glu Thr Asp
            35                  40                  45

Glu Glu Pro Glu Glu Pro Gly Arg Arg Gly Ser Phe Val Glu Met Val
        50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
                100                 105                 110

Tyr Gln Arg Gln Leu Ser Ser Thr Tyr Arg Asp Leu Arg Lys Gly Val
            115                 120                 125

Tyr Val Pro Tyr Thr Gln Gly Lys Trp Glu Gly Glu Leu Gly Thr Asp
        130                 135                 140

Leu Val Ser Ile Pro His Gly Pro Asn Val Thr Val Arg Ala Asn Ile
```

```
                145                 150                 155                 160
Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Ile Ile Gly
            180                 185                 190

Gly Ile Asp His Ser Leu Tyr Thr Gly Ser Leu Trp Tyr Thr Pro Ile
            195                 200                 205

Arg Arg Glu Trp Tyr Tyr Glu Val Ile Ile Val Arg Val Glu Ile Asn
        210                 215                 220

Gly Gln Asp Leu Lys Met Asp Cys Lys Glu Tyr Asn Tyr Asp Lys Ser
225                 230                 235                 240

Ile Val Asp Ser Gly Thr Thr Asn Leu Arg Leu Pro Lys Lys Val Phe
                245                 250                 255

Glu Ala Ala Val Lys Ser Ile Lys Ala Ala Ser Ser Thr Glu Lys Phe
                260                 265                 270

Pro Asp Gly Phe Trp Leu Gly Glu Gln Leu Val Cys Trp Gln Ala Gly
            275                 280                 285

Thr Thr Pro Trp Asn Ile Phe Pro Val Ile Ser Leu Tyr Leu Met Gly
290                 295                 300

Glu Val Thr Asn Gln Ser Phe Arg Ile Thr Ile Leu Pro Gln Gln Tyr
305                 310                 315                 320

Leu Arg Pro Val Glu Asp Val Ala Thr Ser Gln Asp Asp Cys Tyr Lys
                325                 330                 335

Phe Ala Ile Ser Gln Ser Ser Thr Gly Thr Val Met Gly Ala Val Ile
                340                 345                 350

Met Glu Gly Phe Tyr Val Val Phe Asp Arg Ala Arg Lys Arg Ile Gly
            355                 360                 365

Phe Ala Val Ser Ala Cys His Val His Asp Glu Phe Arg Thr Ala Ala
            370                 375                 380

Val Glu Gly Pro Phe Val Thr Leu Asp Met Glu Asp Cys Gly Tyr Asn
385                 390                 395                 400

Ile Pro Gln Thr Asp Glu Ser Thr Leu Met Thr Ile Ala Tyr Val Met
                405                 410                 415

Ala Ala Ile Cys Ala Leu Phe Met Leu Pro Leu Cys Leu Met Val Cys
                420                 425                 430

Gln Trp Arg Cys Leu Arg Cys Leu Arg Gln Gln His Asp Asp Phe Ala
            435                 440                 445

Asp Asp Ile Ser Leu Leu Lys
        450                 455

<210> SEQ ID NO 3
<211> LENGTH: 6
<212> TYPE: PRT
<213> ORGANISM: Artificial Sequence
<220> FEATURE:
<223> OTHER INFORMATION: Distinctive fragment of a BACE455 polypeptide

<400> SEQUENCE: 3

Ile Ala Arg Ile Ile Gly
1               5

<210> SEQ ID NO 4
<211> LENGTH: 7
<212> TYPE: PRT
<213> ORGANISM: Artificial Sequence
<220> FEATURE:
<223> OTHER INFORMATION: Distinctive fragment of a BACE455 polypeptide
```

```
<400> SEQUENCE: 4

Glu Ile Ala Arg Ile Ile Gly
1               5

<210> SEQ ID NO 5
<211> LENGTH: 8
<212> TYPE: PRT
<213> ORGANISM: Artificial Sequence
<220> FEATURE:
<223> OTHER INFORMATION: Distinctive fragment of a BACE455 polypeptide

<400> SEQUENCE: 5

Glu Ile Ala Arg Ile Ile Gly Gly
1               5

<210> SEQ ID NO 6
<211> LENGTH: 8
<212> TYPE: PRT
<213> ORGANISM: Artificial Sequence
<220> FEATURE:
<223> OTHER INFORMATION: Distinctive fragment of a BACE455 polypeptide

<400> SEQUENCE: 6

Ala Glu Ile Ala Arg Ile Ile Gly
1               5

<210> SEQ ID NO 7
<211> LENGTH: 9
<212> TYPE: PRT
<213> ORGANISM: Artificial Sequence
<220> FEATURE:
<223> OTHER INFORMATION: Distinctive fragment of a BACE455 polypeptide

<400> SEQUENCE: 7

Ala Glu Ile Ala Arg Ile Ile Gly Gly
1               5

<210> SEQ ID NO 8
<211> LENGTH: 10
<212> TYPE: PRT
<213> ORGANISM: Artificial Sequence
<220> FEATURE:
<223> OTHER INFORMATION: Distinctive fragment of a BACE455 polypeptide

<400> SEQUENCE: 8

Ala Glu Ile Ala Arg Ile Ile Gly Gly Ile
1               5                   10

<210> SEQ ID NO 9
<211> LENGTH: 9
<212> TYPE: PRT
<213> ORGANISM: Artificial Sequence
<220> FEATURE:
<223> OTHER INFORMATION: Distinctive fragment of a BACE455 polypeptide

<400> SEQUENCE: 9

Tyr Ala Glu Ile Ala Arg Ile Ile Gly
1               5

<210> SEQ ID NO 10
<211> LENGTH: 10
<212> TYPE: PRT
<213> ORGANISM: Artificial Sequence
<220> FEATURE:
<223> OTHER INFORMATION: Distinctive fragment of a BACE455 polypeptide
```

```
<400> SEQUENCE: 10

Tyr Ala Glu Ile Ala Arg Ile Ile Gly Gly
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Distinctive fragment of a BACE455 polypeptide

<400> SEQUENCE: 11

Tyr Ala Glu Ile Ala Arg Ile Ile Gly Gly Ile
1               5                   10

<210> SEQ ID NO 12
<211> LENGTH: 18
<212> TYPE: DNA
<213> ORGANISM: Artificial Sequence
<220> FEATURE:
<223> OTHER INFORMATION: probe

<400> SEQUENCE: 12
attgccagga tcattgga                                                 18

<210> SEQ ID NO 13
<211> LENGTH: 10
<212> TYPE: DNA
<213> ORGANISM: Artificial Sequence
<220> FEATURE:
<223> OTHER INFORMATION: primer

<400> SEQUENCE: 13
aggcatcctg                                                          10

<210> SEQ ID NO 14
<211> LENGTH: 10
<212> TYPE: DNA
<213> ORGANISM: Artificial Sequence
<220> FEATURE:
<223> OTHER INFORMATION: primer

<400> SEQUENCE: 14
gggctggcct                                                          10

<210> SEQ ID NO 15
<211> LENGTH: 10
<212> TYPE: DNA
<213> ORGANISM: Artificial Sequence
<220> FEATURE:
<223> OTHER INFORMATION: primer

<400> SEQUENCE: 15
atgctgagat                                                          10

<210> SEQ ID NO 16
<211> LENGTH: 6
<212> TYPE: DNA
<213> ORGANISM: Artificial Sequence
<220> FEATURE:
<223> OTHER INFORMATION: primer

<400> SEQUENCE: 16 tgccag                                                               6
```

```
<210> SEQ ID NO 17
<211> LENGTH: 6
<212> TYPE: DNA
<213> ORGANISM: Artificial Sequence
<220> FEATURE:
<223> OTHER INFORMATION: primer

<400> SEQUENCE: 17 gatcat                                                                    6

<210> SEQ ID NO 18
<211> LENGTH: 10
<212> TYPE: DNA
<213> ORGANISM: Artificial Sequence
<220> FEATURE:
<223> OTHER INFORMATION: primer

<400> SEQUENCE: 18
tggaggtatc                                                               10

<210> SEQ ID NO 19
<211> LENGTH: 10
<212> TYPE: DNA
<213> ORGANISM: Artificial Sequence
<220> FEATURE:
<223> OTHER INFORMATION: primer

<400> SEQUENCE: 19
gaccactcgc                                                               10

<210> SEQ ID NO 20
<211> LENGTH: 10
<212> TYPE: DNA
<213> ORGANISM: Artificial Sequence
<220> FEATURE:
<223> OTHER INFORMATION: primer

<400> SEQUENCE: 20
tgtacacagg                                                               10

<210> SEQ ID NO 21
<211> LENGTH: 10
<212> TYPE: DNA
<213> ORGANISM: Artificial Sequence
<220> FEATURE:
<223> OTHER INFORMATION: primer

<400> SEQUENCE: 21
cagtctctgg                                                               10

<210> SEQ ID NO 22
<211> LENGTH: 6
<212> TYPE: DNA
<213> ORGANISM: Artificial Sequence
<220> FEATURE:
<223> OTHER INFORMATION: primer

<400> SEQUENCE: 22 caggat                                                                    6

<210> SEQ ID NO 23
<211> LENGTH: 8
<212> TYPE: DNA
<213> ORGANISM: Artificial Sequence
<220> FEATURE:
<223> OTHER INFORMATION: primer
```

```
<400> SEQUENCE: 23 ccaggatc                                                            8

<210> SEQ ID NO 24
<211> LENGTH: 10
<212> TYPE: DNA
<213> ORGANISM: Artificial Sequence
<220> FEATURE:
<223> OTHER INFORMATION: primer

<400> SEQUENCE: 24
gccaggatca                                                         10

<210> SEQ ID NO 25
<211> LENGTH: 18
<212> TYPE: DNA
<213> ORGANISM: Artificial Sequence
<220> FEATURE:
<223> OTHER INFORMATION: primer

<400> SEQUENCE: 25
attgccagga tcattgga                                                18

<210> SEQ ID NO 26
<211> LENGTH: 21
<212> TYPE: DNA
<213> ORGANISM: Artificial Sequence
<220> FEATURE:
<223> OTHER INFORMATION: primer

<400> SEQUENCE: 26
tgactgggaa cacccccataa c                                           21

<210> SEQ ID NO 27
<211> LENGTH: 19
<212> TYPE: DNA
<213> ORGANISM: Artificial Sequence
<220> FEATURE:
<223> OTHER INFORMATION: primer

<400> SEQUENCE: 27
agttgtgcat gggagcgag                                               19

<210> SEQ ID NO 28
<211> LENGTH: 19
<212> TYPE: DNA
<213> ORGANISM: Artificial Sequence
<220> FEATURE:
<223> OTHER INFORMATION: primer

<400> SEQUENCE: 28
cccgcagacg ctcaacatc                                               19

<210> SEQ ID NO 29
<211> LENGTH: 21
<212> TYPE: DNA
<213> ORGANISM: Artificial Sequence
<220> FEATURE:
<223> OTHER INFORMATION: primer

<400> SEQUENCE: 29
cagcgagtgg tcgatacctc c                                            21

<210> SEQ ID NO 30
<211> LENGTH: 24
```

```
<212> TYPE: DNA
<213> ORGANISM: Artificial Sequence
<220> FEATURE:
<223> OTHER INFORMATION: primer

<400> SEQUENCE: 30
gcggatccac catggcccaa gccc                                              24

<210> SEQ ID NO 31
<211> LENGTH: 33
<212> TYPE: DNA
<213> ORGANISM: Artificial Sequence
<220> FEATURE:
<223> OTHER INFORMATION: primer

<400> SEQUENCE: 31
ggggaattca cttcagcagg gagatgtcat cag                                    33

<210> SEQ ID NO 32
<211> LENGTH: 10
<212> TYPE: PRT
<213> ORGANISM: Artificial Sequence
<220> FEATURE:
<223> OTHER INFORMATION: fluorogenic App-based peptide MCA

<400> SEQUENCE: 32

Ser Glu Val Asn Leu Asp Ala Glu Phe Lys
1               5                   10

<210> SEQ ID NO 33
<211> LENGTH: 9
<212> TYPE: PRT
<213> ORGANISM: Artificial Sequence
<220> FEATURE:
<223> OTHER INFORMATION: BACE inhibitor III
<220> FEATURE:
<221> NAME/KEY: MISC_FEATURE
<222> LOCATION: (5)..(5)
<223> OTHER INFORMATION: Xaa is statine

<400> SEQUENCE: 33

His Glu Val Asn Xaa Val Ala Glu Phe
1               5

<210> SEQ ID NO 34
<211> LENGTH: 7
<212> TYPE: PRT
<213> ORGANISM: Artificial Sequence
<220> FEATURE:
<223> OTHER INFORMATION: APP sequence near the beta-secretase cleavage
      site

<400> SEQUENCE: 34

Glu Val Lys Met Asp Ala Glu
1               5

<210> SEQ ID NO 35
<211> LENGTH: 8
<212> TYPE: PRT
<213> ORGANISM: Homo sapiens

<400> SEQUENCE: 35

Leu Val Asn Met Ala Glu Gly Asp
1               5

<210> SEQ ID NO 36
<211> LENGTH: 501
```

-continued

```
<212> TYPE: PRT
<213> ORGANISM: Homo sapiens

<400> SEQUENCE: 36

Met Ala Gln Ala Leu Pro Trp Leu Leu Leu Trp Met Gly Ala Gly Val
1               5                   10                  15

Leu Pro Ala His Gly Thr Gln His Gly Ile Arg Leu Pro Leu Arg Ser
                20                  25                  30

Gly Leu Gly Gly Ala Pro Leu Gly Leu Arg Leu Pro Arg Glu Thr Asp
            35                  40                  45

Glu Glu Pro Glu Glu Pro Gly Arg Arg Gly Ser Phe Val Glu Met Val
50                  55                  60

Asp Asn Leu Arg Gly Lys Ser Gly Gln Gly Tyr Tyr Val Glu Met Thr
65                  70                  75                  80

Val Gly Ser Pro Pro Gln Thr Leu Asn Ile Leu Val Asp Thr Gly Ser
                85                  90                  95

Ser Asn Phe Ala Val Gly Ala Ala Pro His Pro Phe Leu His Arg Tyr
            100                 105                 110

Tyr Gln Arg Gln Leu Ser Ser Thr Tyr Arg Asp Leu Arg Lys Gly Val
        115                 120                 125

Tyr Val Pro Tyr Thr Gln Gly Lys Trp Glu Gly Glu Leu Gly Thr Asp
130                 135                 140

Leu Val Ser Ile Pro His Gly Pro Asn Val Thr Val Arg Ala Asn Ile
145                 150                 155                 160

Ala Ala Ile Thr Glu Ser Asp Lys Phe Phe Ile Asn Gly Ser Asn Trp
                165                 170                 175

Glu Gly Ile Leu Gly Leu Ala Tyr Ala Glu Ile Ala Arg Pro Asp Asp
            180                 185                 190

Ser Leu Glu Pro Phe Phe Asp Ser Leu Val Lys Gln Thr His Val Pro
        195                 200                 205

Asn Leu Phe Ser Leu Gln Leu Cys Cys Ala Gly Phe Pro Leu Asn Gln
210                 215                 220

Ser Glu Val Leu Ala Ser Val Gly Gly Ser Met Ile Ile Gly Gly Ile
225                 230                 235                 240

Asp His Ser Leu Tyr Thr Gly Ser Leu Trp Tyr Thr Pro Ile Arg Arg
                245                 250                 255

Glu Trp Tyr Tyr Glu Val Ile Ile Val Arg Val Glu Ile Asn Gly Gln
            260                 265                 270

Asp Leu Lys Met Asp Cys Lys Glu Tyr Asn Tyr Asp Lys Ser Ile Val
        275                 280                 285

Asp Ser Gly Thr Thr Asn Leu Arg Leu Pro Lys Lys Val Phe Glu Ala
290                 295                 300

Ala Val Lys Ser Ile Lys Ala Ala Ser Ser Thr Glu Lys Phe Pro Asp
305                 310                 315                 320

Gly Phe Trp Leu Gly Glu Gln Leu Val Cys Trp Gln Ala Gly Thr Thr
                325                 330                 335

Pro Trp Asn Ile Phe Pro Val Ile Ser Leu Tyr Leu Met Gly Glu Val
            340                 345                 350

Thr Asn Gln Ser Phe Arg Ile Thr Ile Leu Pro Gln Gln Tyr Leu Arg
        355                 360                 365

Pro Val Glu Asp Val Ala Thr Ser Gln Asp Asp Cys Tyr Lys Phe Ala
370                 375                 380

Ile Ser Gln Ser Ser Thr Gly Thr Val Met Gly Ala Val Ile Met Glu
385                 390                 395                 400
```

```
Gly Phe Tyr Val Val Phe Asp Arg Ala Arg Lys Arg Ile Gly Phe Ala
                405                 410                 415
Val Ser Ala Cys His Val His Asp Glu Phe Arg Thr Ala Ala Val Glu
            420                 425                 430
Gly Pro Phe Val Thr Leu Asp Met Glu Asp Cys Gly Tyr Asn Ile Pro
        435                 440                 445
Gln Thr Asp Glu Ser Thr Leu Met Thr Ile Ala Tyr Val Met Ala Ala
    450                 455                 460
Ile Cys Ala Leu Phe Met Leu Pro Leu Cys Leu Met Val Cys Gln Trp
465                 470                 475                 480
Arg Cys Leu Arg Cys Leu Arg Gln Gln His Asp Asp Phe Ala Asp Asp
            485                 490                 495
Ile Ser Leu Leu Lys
            500
```